(12) United States Patent
Taguchi

(10) Patent No.: US 12,171,810 B2
(45) Date of Patent: Dec. 24, 2024

(54) ANGIOGENESIS PROMOTER AND THERAPEUTIC METHOD

(71) Applicant: NATIONAL INSTITUTE FOR MATERIALS SCIENCE, Tsukuba (JP)

(72) Inventor: Tetsushi Taguchi, Tsukuba (JP)

(73) Assignee: National Institute for Materials Science, Tsukuba (JP)

( * ) Notice: Subject to any disclaimer, the term of this patent is extended or adjusted under 35 U.S.C. 154(b) by 761 days.

(21) Appl. No.: 17/281,718

(22) PCT Filed: Oct. 2, 2019

(86) PCT No.: PCT/JP2019/038933
§ 371 (c)(1),
(2) Date: Mar. 31, 2021

(87) PCT Pub. No.: WO2020/071429
PCT Pub. Date: Apr. 9, 2020

(65) Prior Publication Data
US 2021/0386833 A1    Dec. 16, 2021

(30) Foreign Application Priority Data

Oct. 4, 2018  (JP) ................................ 2018-189217

(51) Int. Cl.
*A61K 38/39* (2006.01)
*A61K 35/60* (2006.01)
*A61P 9/00* (2006.01)

(52) U.S. Cl.
CPC ............... *A61K 38/39* (2013.01); *A61K 35/60* (2013.01); *A61P 9/00* (2018.01)

(58) Field of Classification Search
None
See application file for complete search history.

(56) References Cited

U.S. PATENT DOCUMENTS

| | | | |
|---|---|---|---|
| 2004/0009589 A1* | 1/2004 | Levenberg ............. | C12N 5/069 435/366 |
| 2005/0239897 A1* | 10/2005 | Pittenger ................. | A61P 17/02 514/569 |
| 2009/0269404 A1 | 10/2009 | Ishiguro et al. | |
| 2019/0247537 A1 | 8/2019 | Taguchi | |
| 2019/0336642 A1* | 11/2019 | Taguchi ................. | A61L 24/102 |
| 2020/0206382 A1 | 7/2020 | Taguchi et al. | |

FOREIGN PATENT DOCUMENTS

| | | |
|---|---|---|
| JP | 2007-070309 A | 3/2007 |
| JP | 2014-005211 A | 1/2014 |
| JP | 2019-051189 A | 4/2019 |
| WO | WO 2008/016163 A1 | 2/2008 |
| WO | WO 2015/076252 A1 | 5/2015 |
| WO | WO-2017126390 A1 * | 7/2017 ......... A61L 24/0005 |
| WO | WO 2018/079538 | 5/2018 |
| WO | 2019-045081 A1 | 3/2019 |
| WO | 2019-181294 A1 | 9/2019 |

OTHER PUBLICATIONS

Partial Supplementary European Search Report in Europe Application No. 19868467.2, dated Oct. 18, 2022, 24 pages.
Ryo Mizuta et al: "Enhanced Sealing by Hydrophobic Modification of Alaska Pollock-Derived Gelatin-Based Surgical Sealants for the Treatment of Pulmonary Air Leaks", Macromolecular Bioscience, vol. 17, No. 4, Nov. 15, 2016 (Nov. 15, 2016), p. 1600349, XP055581004.
International Preliminary Report on Patentability, with English translation of Written Opinion, for Application No. PCT/JP2019/038933, dated Mar. 23, 2021, 13 pages.
D. J. Collinson et al. "Therapeutic Angiogenesis in Peripheral Arterial Disease: Can Biotechnology Produce an Effective Collateral Circulation", European Journal of Vascular & AMP; Endovascular Surgery vol. 28, No. 1, Jul. 1, 2004 (Jul. 1, 2004). pp. 9-23, XP0555344.22, Amsterdam, NL, ISSN: 1078-5884, DOI: 10.1016/~.ejvs 2004.03.021.
Extended European Search Report from EP 19 86 8467.2, dated Jan. 3, 2023, 31 pages.
Sunil R. Iyer et al. "Therapeutic Angiogenesis for Peripheral Artery Disease", JACC: Basic to Translational Science, vol. 2, No. 5, Oct. 1, 2017 (Oct. 1, 2017), pp. 503-512, XP055953677, ISSN: 2452-302X, DOI: 10.1016/j.jacbts.2017.07.012.
Takei, Takayuki et al., Lecture abstracts of the autumn research presentation meeting of the Society of Chemical Engineers, Japan, 2012, 44th, V304, English translation.
Mizuta, Ryo et al., Polymers, The Society of Polymer Science, Japan, 2017, vol. 66, No. 9, pp. 490-493, English translation.
Yoshizawa, K. et al., "Enhanced angiogenesis of growth factor-free porous biodegradable adhesive made with hexahoyl group-modified gelatin.", Biomaterials, 2015, vol. 63, pp. 14-23.
Mizuno, Y. et al., J Tissue Eng Regen Med., Sep. 2019, DOI:10.1002/term.2957 pp. 1-9.

(Continued)

Primary Examiner — Jennifer A Berrios
(74) Attorney, Agent, or Firm — Crowell & Moring LLP

(57) ABSTRACT

The present invention addresses the problem of providing an angiogenesis promoter capable of exerting an excellent angiogenesis promoting effect without containing any growth factor. The present invention also addresses the problem of providing a therapeutic method. An angiogenesis promoter that comprises as an active ingredient at least one member selected from the group consisting of a gelatin derivative represented by formula 1 and a crosslinked product of the gelatin derivative:

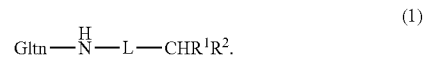

(1)

In formula 1: Gltn represents a gelatin residue; L represents a single bond or a divalent linking group; and $R^1$ and $R^2$ independently represent a hydrocarbon group having 1-20 carbon atoms or a hydrogen atom, provided that at least one of $R^1$ and $R^2$ represents the aforesaid hydrocarbon group.

7 Claims, 15 Drawing Sheets

(56) References Cited

OTHER PUBLICATIONS

International Search Report in Application No. PCT/JP2019/038933, dated Dec. 24, 2019, 2 pages.
Ikeda, Uichi, Series: Arteriosclerosis obliterans (ASO) learned from the basics, ASO treatment—(4) Angiogenic therapy, Thrombosis and Circulation, 2014, vol. 22, No. 2, pp. 345-347, 5 pages.

* cited by examiner

PBS

Org

34C12

*: Implanted site
Green arrow: blood vessel
Red arrow: blood vessel

Org

33C12

PBS

Org

33C12

Org

26C16

Sham

Org

41C8

33C12

26C16

ANGIOGENESIS PROMOTER AND THERAPEUTIC METHOD

This application is a 371 application of PCT/JP2019/038933 having an international filing date of Oct. 2, 2019, which claims priority to JP2018-189217 filed Oct. 4, 2018, the enter content of each of which is incorporated herein by reference.

TECHNICAL FIELD

The present invention relates to an angiogenesis promoter, and a therapeutic method.

BACKGROUND ART

As the treatment of peripheral artery disease (PAD) and the like, known are methods of administering a growth factor such as fibroblast growth factor (FGF) to a patient to promote angiogenesis in the patient.

For example, Patent Document 1 describes a preparation for releasing a bioactive factor, wherein the bioactive factor is supported on a "multi-layered structure of crosslinked gelatin gel having a layered structure wherein plural layers of crosslinked gelatin gel by irradiating gelatin or a gelatin derivative with electron beam under an oxygen-containing atmosphere are arranged adjoiningly to each other."

PRIOR ART DOCUMENT

Patent Document

Patent Document 1: International Publication No. WO2008/016163

SUMMARY OF INVENTION

Technical Problem

Patent Document 1 demonstrates in animal experiments that the preparation for releasing a bioactive factor promotes angiogenesis. However, according to the present inventors' study, bioactive factors (e.g. growth factor) have problems that they are expensive and not always sufficiently stable. The preparation for releasing a bioactive factor described in Patent Document 1 contains a growth factor that is expensive and may not exhibit an intended therapeutic effect, and there is therefore need for improvements.

Accordingly, an object of the present invention is to provide an angiogenesis promoter that can exert an excellent angiogenesis promoting action even without any growth factor. Another object of the present invention is also to provide a method for promoting angiogenesis without administering a growth factor, and a method of treating thereby a peripheral artery disease (PAD) and the like.

Solution to Problem

The present inventors have conducted intensive researches to achieve the above-described objects, and as a result, have found that the objects can be achieved with a specific gelatin derivative or a crosslinked product thereof.

[1] An angiogenesis promoter comprising at least one selected from the group consisting of a gelatin derivative represented by formula (1) and a crosslinked product of the gelatin derivative as an active ingredient:

wherein Gltn represents a gelatin residue; L represents a single bond or a divalent linking group; $R^1$ and $R^2$ are each independently a hydrocarbon group having 1 to 20 carbon atoms, or a hydrogen atom, provided that at least one selected from the group consisting of $R^1$ and $R^2$ is the hydrocarbon group.

[2] The angiogenesis promoter according to [1], wherein the angiogenesis promoter is substantially free of a growth factor.

[3] The angiogenesis promoter according to [1] or [2], wherein the hydrocarbon group is at least one selected from the group consisting of a linear hydrocarbon group having 2 to 20 carbon atoms, an alicyclic hydrocarbon group having 2 to 20 carbon atoms, an aromatic hydrocarbon group having 6 to 14 carbon atoms, and a combination group thereof having 2 to 20 carbon atoms.

[4] The angiogenesis promoter according to any of [1] to [3], wherein the gelatin derivative is derived from a cold-water fish.

[5] The angiogenesis promoter according to [4], wherein the cold-water fish is a cod.

[6] The angiogenesis promoter according to any of [1] to [5], wherein the angiogenesis promoter comprises a cross-linked product of the gelatin derivative as an active ingredient.

[7] The angiogenesis promoter according to any of [1] to [6], wherein the angiogenesis promoter is in a form of a fiber mesh.

[8] The angiogenesis promoter according to any of [1] to [6], wherein the angiogenesis promoter is in a form of particles.

[9] The angiogenesis promoter according to any of [1] to [8], wherein the angiogenesis promoter is used for treating a peripheral artery disease.

[10] A method for promoting angiogenesis, comprising administering a pharmaceutically effective amount of the angiogenesis promoter according to any of [1] to [8] to a mammal subject.

[11] A method for treating a peripheral artery disease in a mammal, comprising administering a pharmaceutically effective amount of the angiogenesis promoter according to any of [1] to [8] to an affected area of a mammal in need thereof.

[12] The angiogenesis promoter according to any of [1] to [8], wherein the angiogenesis promoter is used for treating a peripheral artery disease.

[13] Use of at least one selected from the group consisting of a gelatin derivative represented by formula (1) and a crosslinked product of the gelatin derivative, for preparing an angiogenesis promoter:

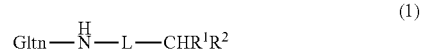

wherein Gltn represents a gelatin residue; L represents a single bond or a divalent linking group; $R^1$ and $R^2$ are each independently a hydrocarbon group having 1 to 20 carbon atoms, or a hydrogen atom, provided that at least one selected from the group consisting of $R^1$ and $R^2$ is the hydrocarbon group.

[14] The use according to [13], wherein the angiogenesis promoter is a medicament for treating a peripheral artery disease.

[15] The use according to [13] or [14], wherein the angiogenesis promoter is substantially free of a growth factor.

[16] The use according to any of [13] to [15], wherein the hydrocarbon group is at least one selected from the group consisting of a linear hydrocarbon group having 2 to 20 carbon atoms, an alicyclic hydrocarbon group having 2 to 20 carbon atoms, an aromatic hydrocarbon group having 6 to 14 carbon atoms, and a combination group thereof having 2 to 20 carbon atoms.

[17] The use according to any of [13] to [16], wherein the gelatin derivative is derived from a cold-water fish.

[18] The use according to [17], wherein the cold-water fish is a cod.

[19] The use according to any of [13] to [18], wherein the crosslinked product of the gelatin derivative is contained as an active ingredient.

[20] The use according to any of [13] to [19], wherein the angiogenesis promoter is in a form of a fiber mesh.

[21] The use according to any of [13] to [19], wherein the angiogenesis promoter is in a form of particles.

Advantageous Effects of Invention

According to the present invention, a novel angiogenesis promoter, a novel method for promoting angiogenesis, and a novel method for treating a peripheral artery disease (PAD) can be provided.

DESCRIPTION OF EMBODIMENTS

Figure 1:
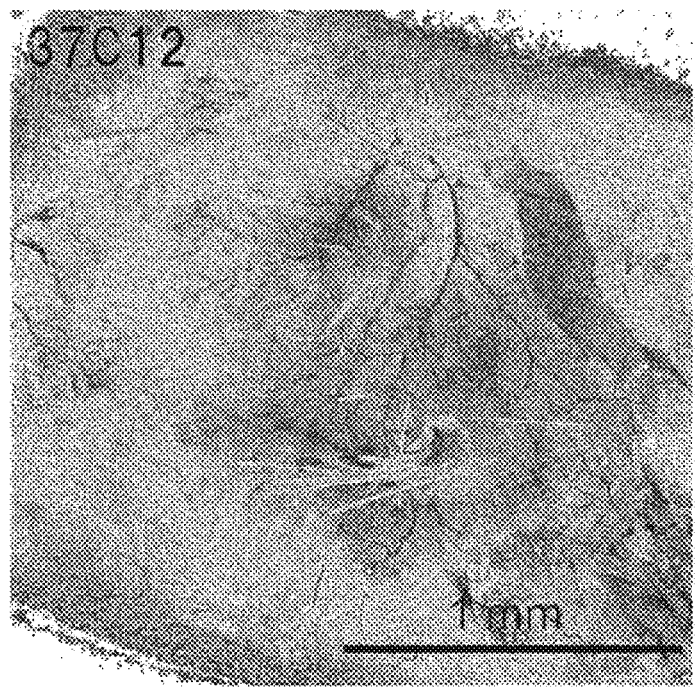
FIG. 1 is a photograph showing a tissue around the site of a rat into which a solution of "37C12-ApGltn" was subcutaneously injected at a solid content of 20% (mass/volume), wherein the photograph was taken 3 days after the injection. To prepare "37C12-ApGltn", Alaska pollock gelatin was used as a raw material, and dodecyl groups were introduced to 37 mol % of the amino groups of the Alaska pollock gelatin by the method described below.

Hereinafter, the present invention is described in detail.

The following description may be made based on representative embodiments of the present invention, but the present invention is not limited to such embodiments.

As used herein, the numerical range expressed with "to" means a range including the numerical values described before and after "to" as the lower limit value and the upper limit value.

[Angiogenesis Promoter]

According to an embodiment of the present invention, an angiogenesis promoter comprises at least one selected from the group consisting of a gelatin derivative represented by formula (1) and a crosslinked product of the gelatin derivative as an active ingredient.

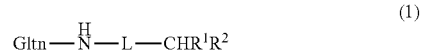

$$\text{Gltn}-\overset{H}{N}-L-CHR^1R^2 \qquad (1)$$

In formula (1), Gltn represents a gelatin residue; L represents a single bond or a divalent linking group; $R^1$ and $R^2$ are each independently a hydrocarbon group having 1 to 20 carbon atoms, or a hydrogen atom, provided that at least one selected from the group consisting of $R^1$ and $R^2$ is the hydrocarbon group.

An angiogenesis promoter according to an embodiment of the present invention comprises a gelatin derivative modified by a predetermined substituent and/or a crosslinked product thereof (hereinafter, these are sometimes collectively referred to as "gelatin derivative or the like"). Such an angiogenesis promoter can be used typically by being mixed with a predetermined amount of water, gelated, and then injected transdermally into a site of interest (affected area) in a patient.

Gelatin means a degenerated collagen in which three-dimensional triple helix structures are collapsed. Gelatin is highly biocompatible and has already been used as a variety of medical materials in clinical practice.

On the other hand, the gelatin derivative described above has a specific substituent group, and the present inventors have found that an angiogenesis promoter comprising such a gelatin derivative or the like as an active ingredient, typically as injected into a living body after gelatinization, surprisingly exhibits an angiogenesis promoting action in vivo in cells around the site into which the gel was injected.

As demonstrated in the Examples described below, not only expression of angiogenesis markers but also expression of cell growth factors has been confirmed in cells around the site into which the gel was injected. Without wishing to be bound by any theory, the present inventors presume a mechanism exhibiting the angiogenic effect as follows.

That is, an angiogenesis promoter according to an embodiment of the present invention comprises a gelatin derivative or the like having a specific substituent group, and cells around the site into which the angiogenesis promoter has been injected, tend to be induced to release inflammatory cytokines. As a result, cells around the site of interest produce growth factors such as a vascular endothelial cell growth factor (VEGF) and a tumor necrosis factor (TNF), and angiogenesis is sufficiently promoted even if the gel itself contains no growth factors.

Also, as described above, since the angiogenesis promoter (typically as gelated and then injected) allows utilization of a vascular endothelial cell growth factor (VEGF) or the like produced by cells around the site of interest, the angiogenesis promoter is expected to more stably exhibit the therapeutic effect even if it contains no growth factors.

FIG. 1 is a photograph showing a tissue around the implanted site of a rat, into which a "37C12-ApGltn" gel was subcutaneously injected at a solid content of 20% (mass/volume), 3 days after the injection. To prepare "37C12-ApGltn", dodecyl groups were introduced to 37 mol % of the amino groups of Alaska Pollock gelatin used as a raw material of gelatin by the method described below.

Figure 2:
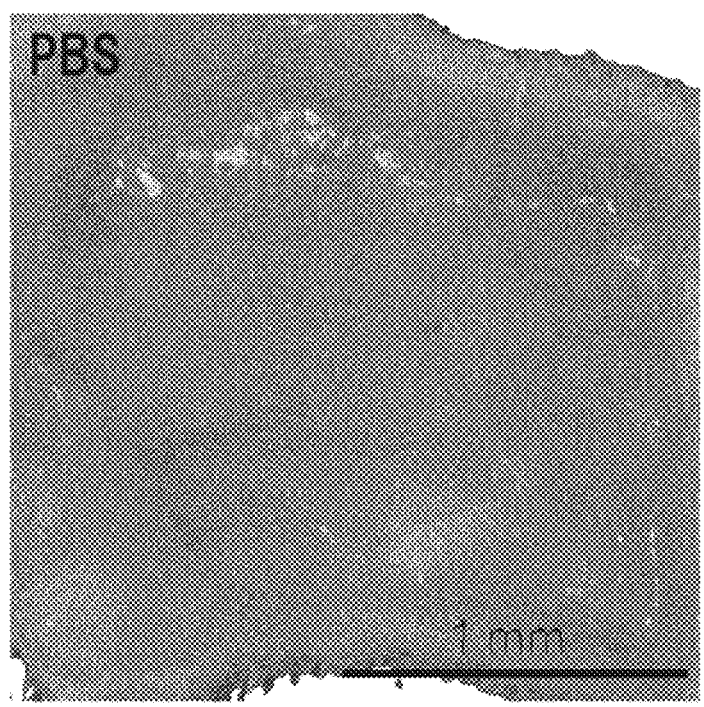
FIG. 2 is a photograph showing a tissue around the site where phosphate buffered saline was injected as a control for the test of FIG. 1, wherein the photograph was taken 3 days after the injection.

Compared to the photograph of FIG. 2, which shows a tissue around the site into which phosphate buffered saline (PBS) was injected as a control, it is found that "37C12-ApGltn", a gel comprising an angiogenesis promoter according to an embodiment of the present invention, resulted in more angiogenesis on day 3 after the injection.

It should be noted that, in FIGS. 1 and 2, the parts appeared as black streaks represent blood vessels.

Hereinafter, each component contained in an angiogenesis promoter according to an embodiment of the present invention is described in detail.

(Gelatin Derivative or the Like)

An angiogenesis promoter according to an embodiment of the present invention comprises at least one selected from the group consisting of a gelatin derivative represented by formula (1) and a crosslinked product thereof as an active ingredient.

(1)

In formula (1), Gltn represents a gelatin residue; L represents a single bond or a divalent linking group; $R^1$ and $R^2$ are each independently a hydrocarbon group having 1 to 20 carbon atoms or a hydrogen atom, provided that at least one selected from the group consisting of $R^1$ and $R^2$ is the hydrocarbon group.

Examples of the divalent linking group of L include, but are not particularly limited to, —C(O)—, —C(O)O—, —OC(O)—, —O—, —S—, —N(R)— (R represents a hydrogen atom or a monovalent organic group, preferably a hydrocarbon group having 1 to 20 carbon atoms), an alkylene group (preferably an alkylene group having 2 to 10 carbon atoms), an alkenylene group (preferably an alkenylene group having 2 to 10 carbon atoms), and combinations thereof. Among these, —C(O)— is preferred.

That is, in formula (1), L is preferably a single bond or —C(O)—.

N is not particularly limited, but N is preferably derived from an ε-amino group of lysine (Lys) in the gelatin. Linking *—CHR$^1$R$^2$ to the amino group of lysine via a linking group or without a linking group (in other words, directly) may be performed by methods utilizing so-called reducing (or reductive) amination reaction (with an aldehyde or a ketone) and Schotten-Baumann reaction (with an acid chloride), which will be described in detail later.

In another embodiment, N may be from a group obtained by reacting a compound having an amino group with a carboxy group of an amino acid in the gelatin using a carbodiimide compound or the like.

One of $R^1$ and $R^2$ is preferably a hydrogen atom.

The —NH— structure in formula (1) can be detected, for example, by a band near 3300 cm$^{-1}$ in the Fourier transform infrared absorption (FT-IR) spectrum.

Examples of the hydrocarbon group having 1 to 20 carbon atoms include, but are not particularly limited to, a linear hydrocarbon group having 1 to 20 carbon atoms, an alicyclic hydrocarbon group having 3 to 20 carbon atoms, an aromatic hydrocarbon group having 6 to 14 carbon atoms, and a combination group thereof.

Examples of the linear hydrocarbon group having 1 to 20 carbon atoms include a methyl group, an ethyl group, a n-propyl group, an i-propyl group, a n-butyl group, a 2-methylpropyl group, a 1-methylpropyl group, and a t-butyl group.

Among them, in terms of obtaining an angiogenesis promoter having a more excellent effect, the carbon number of the linear hydrocarbon group is preferably 2 or more, more preferably 3 or more, further preferably 6 or more, particularly preferably 7 or more, most preferably 8 or more, and preferably 19 or less, more preferably 18 or less, further preferably 17 or less, particularly preferably 16 or less, most preferably 15 or less, and furthermost preferably 14 or less.

Especially, when the sum of the carbon numbers of *—CH$_2$R$^1$R$^2$ is 9 to 20, those angiogenesis promoters result in a greater blood flow rate; when 11 to 19, they result in a further greater blood flow rate; when 12 to 18, they result in a still greater blood flow rate; when 12 to 17, they result in a yet greater blood flow rate; when 12 to 16, they result in an even greater blood flow rate; when 12 to 15, they result in a particularly greater blood flow rate; and when 12 to 14, they result in the greatest blood flow rate.

Examples of the alicyclic hydrocarbon group having 3 to 20 carbon atoms include a cyclopropyl group, a cyclopentyl group, a cyclohexyl group, an adamantyl group, and a norbornyl group.

Examples of the aromatic hydrocarbon group having 6 to 14 carbon atoms include, but are not particularly limited to, a phenyl group, a tolyl group, and a naphthyl group.

Examples of the combination group thereof include, but are not particularly limited to, an aralkyl group having 6 to 12 carbon atoms, such as a benzyl group, a phenethyl group, a naphthylmethyl group, and a naphthylethyl group.

In terms of obtaining an angiogenesis promoter in which the gel has a more excellent effect, above all, the hydrocarbon group having 1 to 20 carbon atoms in formula 1 is preferably an alkyl group having 1 to 20 carbon atoms.

The carbon number of the alkyl group is preferably 2 or more, more preferably 3 or more, further preferably 6 or more, still more preferably 7 or more, yet more preferably 8 or more, even more preferably 9 or more, particularly preferably 10 or more, most preferably 11 or more, and preferably 19 or less, more preferably 18 or less, still more preferably 17 or less, yet more preferably 16 or less, even more preferably 15 or less, particularly preferably 14 or less, and most preferably 13 or less.

In terms of obtaining an angiogenesis promoter having a more excellent effect, the gelatin derivative represented by formula (1) is preferably at least one gelatin derivative selected from the group consisting of those represented by formulas (2) and (3), more preferably a gelatin derivative represented by formula (2).

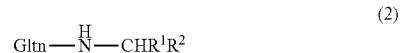

(2)

(3)

In formulas (2) and (3), the meaning of each symbol is the same as in formula (1) which has already been described, and preferable options are also the same as in formula (1).

The gelatin derivatives represented by formulas (2) and (3) are typically those in which *—$CHR^1R^2$ (* represents a bonding position. Hereinafter, the group represented by *—$CHR^1R^2$ is also referred to as a "hydrophobic group.") is bonded to an amino group of lysine.

The introduction amount of the hydrophobic group in the gelatin derivatives represented by formula 2 and formula 3 is not particularly limited, but the molar ratio of the amount of imino groups (—NH—) to which the hydrophobic group is attached to the amount of amino groups in the original gelatin (imino group/amino group) is preferably 0.15 to 0.8, more preferably 0.3 to 0.7.

As used herein, the molar ratio of the "imino group/amino group" described above (in other words, "derivatization rate") means a numerical value determined by quantifying the amounts of amino group in the original gelatin and amino group in the gelatin derivative by 2,4,6-trinitrobenzene sulfonic acid method (TNBS method).

An original gelatin that can be used to produce the gelatin derivative is not particularly limited, and it may be any gelatins obtained from natural origin, by synthesis, fermentation or genetic recombination, or the like. Among them, in terms of obtaining a gel having a more excellent effect, the original gelatin is preferably derived from a mammal or a fish, more preferably from a cold-water fish. Examples of the cold-water fish include salmon, sea bream, and cod, and among them, cod is preferred. As used herein, the "cod" means a generic term for fish species belonging to the Gadinae. Examples thereof include *Gadus macrocephalus*, *Eleginus gracilis*, and *Theragra chalcogramma* (Alaska pollock), and especially, *Theragra chalcogramma* is preferred. As used herein, the "salmon" means a generic term for fish species belonging to the Salmonidae, and, as used herein, the "sea bream" means a generic term for fish species belonging to the Sparidae.

An original gelatin may be a processed gelatin. Examples of the processed gelatin include an acid-processed gelatin, an alkali-processed gelatin, and endotoxin-reduced gelatin, and the processes of these may be combined. Among them, the alkali-processed gelatin is preferred, and endotoxin-reduced gelatin is more preferred.

The molecular weight of an original gelatin is not particularly limited, but in terms of obtaining a gel having a more excellent effect, the weight-average molecular weight (Mw) is preferably 20,000 to 150,000, more preferably 30,000 to 100,000. As used herein, the molecular weight of an original gelatin means a weight-average molecular weight as measured based on standard pullulan by gel permeation chromatography (GPC).

An angiogenesis promoter according to an embodiment of the present invention may comprise a crosslinked product of the gelatin derivative. The gelatin derivative can form a reversible crosslinked structure (physical crosslinking) by intermolecular and/or intramolecular interaction. As used herein, however, the "crosslinked product of a (the) gelatin derivative" does not include a gelatin derivative having the reversible physically crosslinked structure described above, but thus means a crosslinked product of a (the) gelatin derivative obtained by an irreversible crosslinking reaction.

A crosslinked product of a gelatin derivative typically means a reaction product having an irreversible crosslinked structure obtained by imparting energy to the gelatin derivative with heat, light, an energy ray, or the like, and/or obtained by subjecting the gelatin derivative to a crosslinking reaction with a crosslinking agent.

An angiogenesis promoter according to an embodiment of the present invention may comprise a gelatin derivative or a crosslinked product thereof alone, or it may comprise the gelatin derivative and the crosslinked product in combination.

A method for obtaining a crosslinked product of a gelatin derivative by imparting energy to the gelatin derivative is not particularly limited, but examples thereof include a method of irradiating the gelatin derivative with heat, or active light or radiation (e.g., electron rays).

Among them, a method of imparting thermal energy, i.e., heating (or thermal crosslinking) is preferred in terms of more easily obtaining a crosslinked product of the gelatin derivative.

The method of thermally crosslinking the gelatin derivative is not particularly limited, but typical examples thereof include a method of heating the gelatin derivative at 100 to 200° C. for 1 to 8 hours under reduced pressure. By the above, for example, an amino group and another reactive group (such as a carboxy group and a mercapto group) in the gelatin derivative react to form a crosslinked product.

A crosslinked product of a gelatin derivative may be also obtained by reacting the gelatin derivative with a crosslinking agent. Examples of the crosslinking agent include, but are not particularly limited to, genipin, a poly acid activated with N-hydroxysuccinimide or N-sulfoxysuccinimide, an aldehyde compound, an acid anhydride, a dithiocarbonate, and a diisothiocyanate.

As a crosslinking agent, used be can the compounds described in WO 2018/079538, paragraphs 0021 to 0024, the contents of which are incorporated herein by reference.

The crosslinking degree of the above-described crosslinked product cannot be meaningfully specified because the number of amino groups that can be involved in the crosslinking reaction is different depending on the derivatization rates, and the crosslinking degree of 100% defined as the state in which all the amino groups have reacted is different in this sense. In general, a gelatin derivative is thought to become less reactive because of the reduced number of remaining amino groups which have not been subjected to derivatization, and the crosslinking reaction thereof is believed to be terminated after reactions of about 10 to 30% of the number of amino groups of original gelatin by a heating treatment of about 3 hours.

(Forms, Other Components, or the Like)

The form of a gelatin derivative or a crosslinked product thereof is not particularly limited, but in terms of being easier to handle and having excellent dispersibility into a solvent, a gelatin derivative or a crosslinked product thereof is preferably in a form of particles. The particle size of the particles is not particularly limited, but it is generally preferred to be 0.5 to 1000 µm.

They can be also in other forms, such as the forms of granules, a fiber, a sheet, a plate, and a fiber mesh. Among them, a fiber mesh is preferred in terms of forming a vascular network in a wide area in vivo.

An angiogenesis promoter according to an embodiment of the present invention may comprise other pharmaceutically acceptable components (auxiliary agents), and examples of the auxiliary agent include an excipient, a stabilizer, and a buffering agent. An angiogenesis promoter can be formulated into any dosage form, such as a powder, a granule, and a tablet, by known methods.

Examples of the buffering agent include, but are not limited to, sodium phosphate, sodium hydrogen phosphate, sodium dihydrogen phosphate, disodium hydrogen phosphate, sodium acetate, and epsilon-aminocaproic acid.

An angiogenesis promoter according to an embodiment of the present invention may comprise other components. Examples of such components include a tonicity agent such as sodium chloride, potassium chloride, or concentrated glycerin; and a surfactant such as polyoxyethylene sorbitan monooleate, polyoxyl 40 stearate, or polyoxyethylene hardened castor oil.

An angiogenesis promoter according to an embodiment of the present invention may not comprise a growth factor, and according to a preferred embodiment, an angiogenesis promoter is substantially free of a growth factor. The growth factor is a generic term for endogenous proteins that promote cell proliferation and differentiation in the bodies of animals. Examples of the growth factor include, but are not limited to, a vascular endothelial cell growth factor (VEGF), a basic fibroblast growth factor (bFGF), a platelet-derived growth factor (PDGF), and a transforming growth factor β (TGF-β).

As used herein, the "substantially free of a growth factor" means that the content of growth factors is 100 ng/mL or less in relation to the volume of solvent added when gelling an angiogenesis promoter of the present invention. The content of growth factors is preferably 10 ng/mL or less, further preferably 1 ng/mL or less, and particularly preferably zero.

It should be noted that the content of growth factors in the gel is measured by enzyme immunoassay (ELISA method).

[Method for Preparing Angiogenesis Promoter]

A method for preparing an angiogenesis promoter is not particularly limited, and a known method can be used. Examples of the known method can include the methods described in WO 2018/079538, paragraphs 0029 to 0035, the contents of which are incorporated herein by reference.

A method of preparing an angiogenesis promoter according to an embodiment of the present invention typically comprises a step of preparing a gelatin derivative. In the case where an angiogenesis promoter contains a crosslinked product of the gelatin derivative, the preparation method further comprises a step of preparing a crosslinked product of the gelatin derivative. Hereinafter, each step is described in detail.

(Step for Preparing Gelatin Derivative)

(1) Preparation of Aqueous Solution of Original Gelatin

An original gelatin is heated at 40 to 90° C. at an amount of 5 to 50 mass/volume %, and dissolved in a solvent, such as water, an organic solvent, or a mixture of water and an organic solvent, to obtain a gelatin solution. As the water, ultra-pure water, deionized water, distilled water, or the like can be used.

The organic solvent is not particularly limited but includes an alcohol or an ester having 1 to 3 carbon atoms, and preferably ethanol.

(2) Derivatization

To the gelatin solution obtained in (1) above, added is a derivatization reagent having a hydrocarbon group to be introduced, and the reaction is performed by stirring for a predetermined time. As the derivatization reagent, an aldehyde or a ketone having a hydrocarbon group can be used. A compound in which an amino group (for example, a primary amino group) is further bound to a hydrocarbon group can be also used as a derivatization reagent.

When an aldehyde or ketone having a hydrocarbon group is used as a derivatization reagent, a gelatin derivative of formula (1) described above is obtained by a so-called "reducing amination."

Also, when a compound wherein an amino group is bound to a hydrocarbon group is used as a derivatization reagent, a carbodiimide compound can be used to bond the hydrocarbon group to a carboxy group of the gelatin via the amino group, thereby obtaining a gelatin derivative of formula (1) described above.

Examples of the aldehyde or ketone having a hydrocarbon group include, but are not particularly limited to, dodecanal, tetradecanal, and decyl ethyl ketone.

In this case, the reaction temperature is 30 to 80° C., and the reaction time is 0.5 to 12 hours. A gelatin wherein the hydrocarbon group described above is bonded to an amino group of the gelatin via a Schiff base ($-N=CR^1R^2$) can be usually obtained only by stirring. The amount of aldehyde used is preferably 1 to 4 times, more preferably 1 to 2 times the stoichiometric amount that corresponds to a desired derivatization rate.

The Schiff base is then reduced to form a structure of formula (1) described above. As the reducing agent, known reducing agents such as sodium cyanoborohydride ($NaBH_3CN$), sodium triacetoxyborohydride ($NaBH(OAc)_3$), 2-picoline borane, and pyridine borane can be used.

Among these, 2-picoline borane is preferred. Picoline borane is stable, and it enables the reducing amination reaction of aldehyde or ketone to be carried out in an organic solvent by one step (one pot) and can achieve a yield of 80 to 900%.

The amount of 2-picoline borane used is preferably 1 to 3 equivalents in relation to 1 equivalent of a derivatization reagent. The order of addition of the reducing agent and the aldehyde or the like is optional, and either may be added first to a gelatin solution, or both may be added simultaneously.

In another embodiment of the derivatization, Schotten-Baumann reaction can be used. The Schotten-Baumann reaction is a method of reacting a carboxylic acid chloride with an amine in the presence of a base to obtain an amide. The Schotten-Baumann reaction can be used to form an amide bond typically using the ε-amino group of lysine to introduce a predetermined hydrophobic group.

More specifically, a base is added to a gelatin solution, a carboxylic acid chloride is dissolved in an organic solvent, and the resulting two solutions are mixed to generate a condensation reaction.

The base is not particularly limited, and generally a water-soluble base, such as triethylamine, pyridine, or the like can be used as the base.

(3) Purification

A crude of the gelatin derivative is precipitated by adding a large excess of poor solvent such as cold ethanol to the reaction solution obtained in step (2), or adding the reaction solution to cold ethanol. The precipitate was filtered off, and then the filtrate was washed with ethanol or the like to obtain the final product (gelatin derivative).

When obtaining a crosslinked product of the gelatin derivative, the method may further comprise the step described below in addition to the steps described above.

(Step of Obtaining Crosslinked Product of Gelatin Derivative)

The methods of obtaining a crosslinked product of a gelatin derivative have been already described above, and the methods specifically include a method of imparting energy to a gelatin derivative, such as a method of thermally crosslinking a gelatin derivative.

The thermally treating method are not particularly limited, but when an original gelatin has a molecular weight (Mw) of about 100,000, examples include a method of heating gelatin derivatives at 140 to 160° C. for 1 to 6 hours.

In the case where a crosslinked product of a gelatin derivative is made into particles, a step of granulating the gelatin derivative may be performed prior to a crosslinking step. A method of granulating a gelatin derivative may comprise, but are not particularly limited to, dispersing a gelatin derivative into a solvent and granulating the gelatin derivative by a spray drying method. The spray drying method is not particularly limited, and a known method thereof can be used.

In the case where a crosslinked product of a gelatin derivative is made into a fiber, the method may comprise a step of spinning the gelatin derivative prior to a crosslinking step. A method of spinning a gelatin derivative may comprise, but are not particularly limited to, dissolving a gelatin derivative into a solvent (e.g., a mixture of an aqueous organic solvent such as ethanol and water) and extruding the gelatin derivative from a nozzle of a spinning apparatus into a coagulation bath to form a fiber.

In the case where a gelatin derivative or a crosslinked product thereof is made into a fiber mesh, the fiber mesh can be obtained by dissolving the gelatin derivative into a solvent (e.g., a mixture of an aqueous organic solvent such as ethanol and water), applying a high voltage to the resulting solution to charge the gelatin derivative by an electrospinning method, thereby obtaining a fiber, and depositing the fiber to obtain a nonwoven fabric (fiber mesh). When introducing a crosslinked structure, a step of imparting energy is further performed to obtain a nonwoven fabric (fiber mesh) having a crosslinked structure.

A method of charging a gelatin derivative may comprise, joining an electrode connected with a high voltage power supply to the solution or a container containing the solution; and applying a voltage of typically 1 to 100 kV, preferably 5 to 50 kV. The voltage may be DC or AC.

The temperature during the electrospinning is not particularly limited, and it may be adjusted as appropriate depending on the boiling point and volatility of a solvent. In one embodiment, the temperature is preferably 10 to 30° C.

The electrospinning can produce a nonwoven fabric (fiber mesh) without heating a gelatin derivative. As a result, unintentional crosslinking of a gelatin derivative is suppressed, and a biotissue adhesive sheet having a more uniform structure (more uniform fiber diameter or the like) tends to be easily obtained.

The energy imparting step is a step of imparting energy to a nonwoven fabric to obtain a biotissue adhesive sheet. Energy imparting results in an intermolecular and/or intramolecular crosslinking of at least a part of the gelatin derivative to produce a biotissue adhesive sheet having more excellent bulk strength and more excellent water resistance.

Examples of the energy imparted include, but are not particularly limited to, an energy ray, light, and heat. Among them, it is preferred to impart energy by heating in terms of more easily obtaining a biotissue adhesive sheet.

Examples of the method of heating include, but are not particularly limited to, a method of heating a nonwoven fabric under the condition of reduced pressure at 100 to 200° C. for 1 to 8 hours. More specifically, when an original gelatin has a molecular weight (Mw) of about 100,000, the method may comprise a step of heating under the condition of reduced pressure at 140 to 160° C. (e.g., 150° C.) for 1 to 6 hours.

A method for obtaining a crosslinked product of a gelatin derivative preferably includes the following methods:

Preferred Embodiment 1: Method of Obtaining Crosslinked Product of Gelatin Derivative a step of spray-drying a solution of a gelatin derivative to particulate, thereby obtaining gelatin derivative particles; and a step of heating the gelatin derivative at 140 to 160° C. (e.g., 150° C.) under reduced pressure for 1 to 6 hours to obtain a crosslinked product of a gelatin derivative.

Preferred Embodiment 2: Method of Obtaining Crosslinked Product of Gelatin Derivative a step of adding ethanol to an aqueous solution of a gelatin derivative to precipitate the gelatin derivative, thereby obtaining gelatin derivative particles; and a step of lyophilizing the gelatin derivative particles, and then heating them at 140 to 160° C. (e.g., 150° C.) under reduced pressure for 1 to 6 hours to obtain a crosslinked product of the gelatin derivative.

Preferred Embodiment 3: Method of Obtaining Crosslinked Product of Gelatin Derivative a step of dissolving a gelatin derivative in a solvent and discharging the solution from a nozzle of a spinning apparatus into a coagulation bath to form a fiber.

Preferred Embodiment 4: Method of Obtaining Crosslinked Product of Gelatin Derivative a step of dissolving a gelatin derivative in a solvent, applying a high voltage to the resulting solution to charge the gelatin derivative, thereby obtaining a fiber, a step of depositing the resulting fiber to obtain a nonwoven fabric (fiber mesh); and optionally, a step of imparting energy to the nonwoven fabric (fiber mesh) to introduce a crosslinked structure.

[Method for Preparing Hydrogel and Treatment with Hydrogel]

An angiogenesis promoter according to an embodiment of the present invention comprises a gelatin derivative or a crosslinked product thereof and is administered to a subject to promote angiogenesis, for example, for treating a disease for which angiogenesis is desired, such as a peripheral artery disease in a mammal. Accordingly, in one embodiment, the present invention provides a method for promoting angiogenesis, comprising administering an angiogenesis promoter described above to a mammal subject. In another embodiment, the present invention provides a method for treating a peripheral artery disease in a mammal, comprising administering a pharmaceutically effective amount of an angiogenesis promoter described above to an affected area of a mammal in need thereof.

The mammal includes, but are not particularly limited to, human and a livestock. In another embodiment, the mammal may be a non-human mammal.

A method of administering an angiogenesis promoter to an affected area is not particularly limited, but usually comprises mixing an angiogenesis promoter with a solvent and gelating it; and administering the gel preferably transdermally to an affected area.

The administration amount may be appropriately increased or decreased depending on the type of disease, the severity of disease, individual differences of patients, administration manners, administration durations, or the like.

A method of gelating an angiogenesis promoter according to an embodiment of the present invention may comprise mixing the angiogenesis promoter with a solvent.

Typical examples comprise dispersing an angiogenesis promoter into a buffer containing a solvent and a buffering agent (e.g., phosphate buffered saline, which is hereinafter referred to as "PBS").

A gel obtained as described above can be used to be injected into a target site of a patient with a transdermal injection device composed of a syringe and others.

The solvent includes, but are not particularly limited to, water, an organic solvent, or a mixture of water and an organic solvent. The organic solvent includes, but are not particularly limited to, an organic solvent miscible with water, such as ethanol and isopropanol.

The amount of a solvent to be mixed is not particularly limited, but it may be generally adjusted to 50 to 99% by mass relative to the total mass of the resulting gel.

The gel may comprise a solvent alone or two or more solvents in combination. When the gel comprises two or more solvents, the total content of the two or more solvents is within the above range.

An angiogenesis promoter according to an embodiment of the present invention comprises a gelatin derivative having a hydrophobic group and tends to induce inflammatory cytokine production from cells at and around the site of interest into which the promotor was typically transdermally injected after the injection. The angiogenesis promoter therefore exhibits the effect of promoting angiogenesis due to endogenous growth factors produced by the surrounding cells.

Thus, even if the gel itself, which comprises an angiogenesis promoter, comprises no growth factors, it sufficiently promotes angiogenesis, and thus does not need to contain a growth factor, which may be expensive and low stable. Furthermore, the gelatin derivative has cell adhesion property and is therefore characterized by acting as a scaffold for vascular endothelial cell migration and infiltration.

EXAMPLES

Hereinafter, the present invention is described in further detail based on Examples. The materials, amounts, percentages, conditions of process, process procedures, and the like shown in the following Examples can be changed as appropriate, unless departing from the spirit of the present invention. Accordingly, the present invention is not to be construed as limited by the following Examples.

[Preparation of Gelatin Derivative]

Example 1

100 g of gelatin (Mw=33,000, manufactured by Nitta Gelatin Inc.) derived from Alaska pollock was dissolved in 350 mL of water, and 140 mL of ethanol was added to the obtained aqueous solution, and the mixture was stirred at 50° C. Dodecanal ($C_{12}H_{24}O$) at 1.5 equivalent molars to the amino groups of gelatin, which is a stoichiometric amount corresponding to a derivatization rate of 50 mol %, was dissolved in 5 mL of ethanol, and mixed with the gelatin solution. Then, 2-picoline borane at about 1.5 equivalent molars to dodecanal were added, and the mixture was stirred for 18 hours. The reaction solution was added dropwise into a cold ethanol at about 10 times the volume of the reaction solution to re-precipitate the resulting gelatin derivative, and suction filtration was performed. The obtained precipitate was added to a cold ethanol at about 5 times the volume of the resulting precipitate, washed with stirring for 1 hour and then subjected to suction filtration. After repeating this washing three times, the filtrate was dried under vacuum for 2 days to obtain a white gelatin derivative, into which a dodecyl group was introduced, at a yield of about 91.6 (mass/mass) %. The derivatization rate (introduction rate) was confirmed by a colorimetric method with trinitrobenzene sulfonic acid and found to be 19 mol % (0.19).

Hereinafter, the gelatin derivative obtained by the above is referred to as "19C12-ApGltn." Similarly, in the following description, a gelatin derivative is sometimes referred to as ["a"C"b"-ApGltn], wherein "b" represents the sum of the carbon numbers of a hydrophobic group (*—$CHR^1R^2$) in formula (1), and "a" represents an introduction rate (mol %) of the hydrophobic group.

In the following description, a gelatin derivative is sometimes described as "aCb" by omitting the description of the "-ApGltn" part, but it has the same meaning as above.

Examples 2 to 7

The gelatin derivatives 48C6, 30C10, 34C12, 34C14, 24C16, and 9C18 were prepared in the same manner as the gelatin derivative 19C12 described above, except that the linear alkylaldehydes of C6, C10, C12, C14, C16, and C18 each were mixed into a gelatin solution in an amount corresponding to a derivatization rate of 150 mol % to the amino groups of the gelatin, and 2-picoline borane at 1.5 equivalent molars to the added alkylaldehydes was added.

[Evaluation]

The following evaluation tests were performed for each gelatin derivative obtained as described above.

(Measurement of Blood Flow Rate)

Phosphate buffered saline (PBS) was added to each of the gelatin derivatives of Examples 1 to 7 and the original gelatin (Org) to prepare a 20% (mass/volume) hydrogel of each. Phosphate buffered saline (PBS) and each hydrogel were injected subcutaneously to the back of mice, and the blood flow rate was measured with a laser doppler blood flow meter.

Each of the gelatin derivatives and the original gelatin in a powder state was sterilized by irradiation with ultraviolet light for 1 hour. 100 mg of each was dissolved in 500 μl of PBS, and then irradiated with UV for another 1 hour. Mice used were Hos: HR-1 hairless mice.

PBS and each hydrogel were injected at 250 μl each into around the middle of the back of the mice under anesthesia, and 1, 2, 3, 4, and 7 days after the injection, the blood flow rate was measured at the site where the test sample was implanted with a laser doppler blood flow meter. The measurement was performed after fixing the mouse respiration rate (3 times/sec) and laser gain (40) from day 2.

Figure 3:
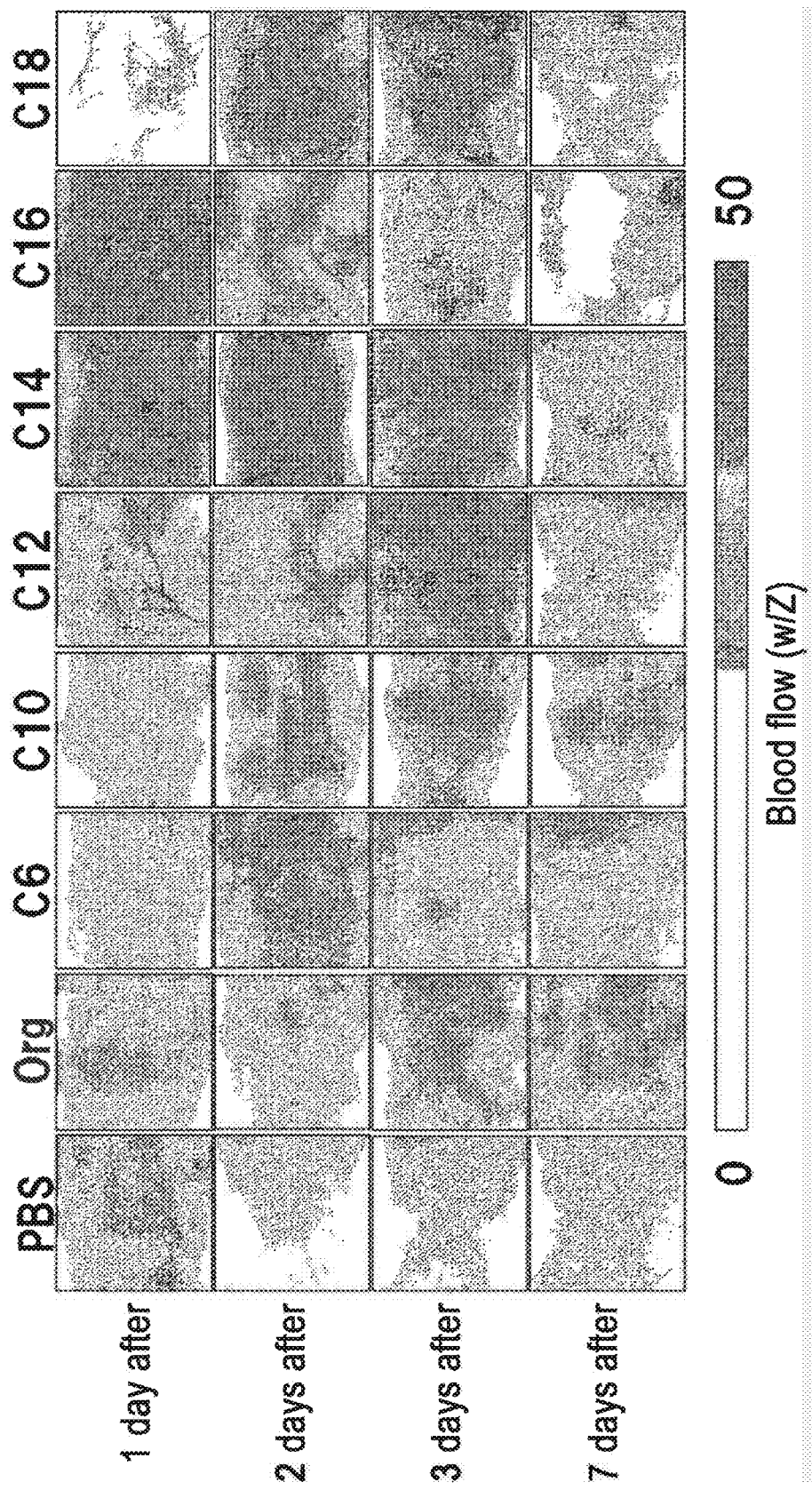
FIG. 3 is blood flow rate images by laser doppler.

Blood flow rate images by the laser doppler on 1, 2, 3, and 7 days are shown in FIG. 3. In FIG. 3, the darkly colored portion indicates that the blood flow rate is greater. In FIG. 3, C6, C10, C12, C14, C16, and C18 correspond to 48C6, 30C10, 34C12, 34C14, 24C16, and 9C18, respectively. The same applies to the descriptions below.

Figure 4:
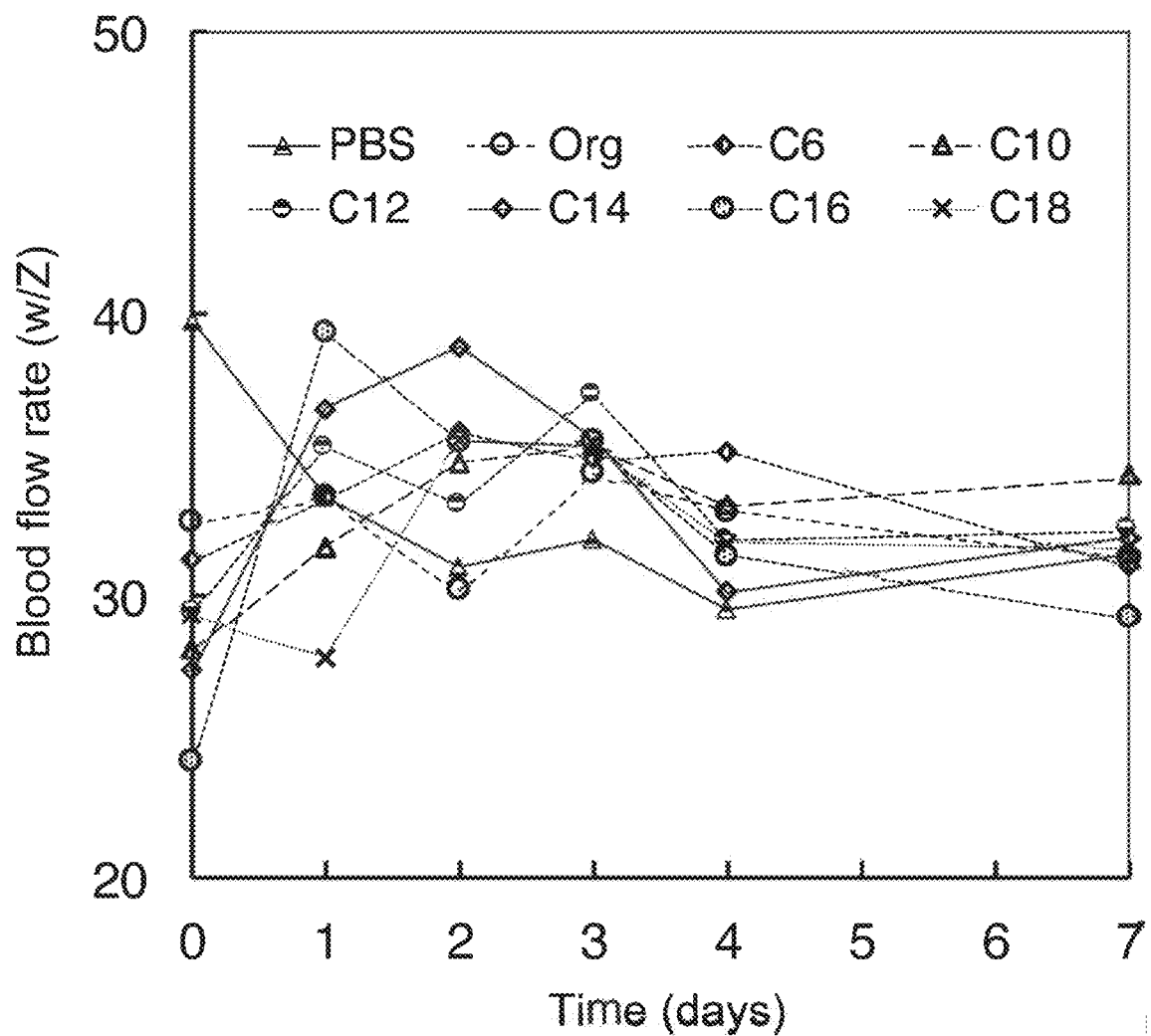
FIG. 4 is the quantification results of blood flow rate by laser doppler.

The quantification results of blood flow rate are shown in FIG. 4.

According to FIGS. 3 and 4, when the gels containing angiogenesis promoters according to embodiments of the present invention was used, an increase in blood flow rate was observed on days 2 to 3 after the injection in all samples. On the other hand, no such effect was obtained when PBS alone was injected or when the original gelatin was injected.

Table 1 shows the blood flow rate in the early stage after the injection (specifically, day 3 after the injection). According to Table 1, the blood flow rate was increased in all the cases the gels containing angiogenesis promoters according to embodiments of the present invention were injected as compared to the case the original gelatin (Org) or control (PBS) was used.

Especially, it was found that when the carbon number of a hydrophobic group was 9 to 20, a greater blood flow rate was obtained; when 11 to 19, a further greater blood flow rate was obtained; when 12 to 18, a still greater blood flow rate was obtained; when 12 to 17, a yet greater blood flow rate was obtained; when 12 to 16, an even greater blood flow rate was obtained; when 12 to 15, a particularly greater blood flow rate was obtained; and when 12 to 14, the greatest blood flow rate was obtained.

TABLE 1

|     | Blood flow rate(day 3) |
| --- | --- |
| PBS | 32.0 |
| Org | 34.3 |
| C6  | 34.8 |
| C10 | 35.3 |
| C12 | 37.3 |
| C14 | 35.6 |
| C16 | 35.5 |
| C18 | 35.4 |

(Tissue Observation 1)

In the same manner as in the measurement of blood flow rate described above, a 34C14-ApGltn gel was implanted subcutaneously into the back of the mouse, and 2 days after, a tissue around the implanted site was extracted and observed.

Figure 5:
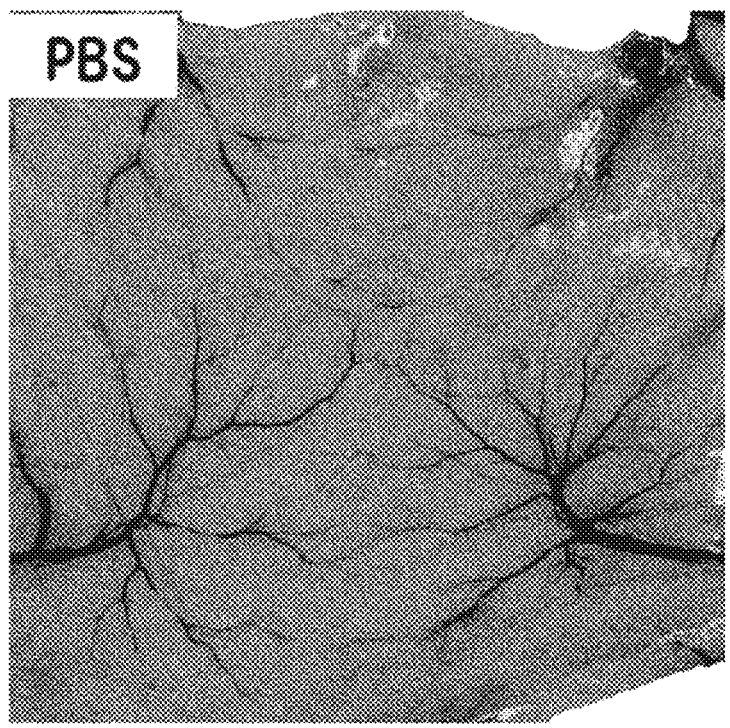
FIG. 5 is a photograph of the tissue into which PBS alone was injected.
Figure 6:
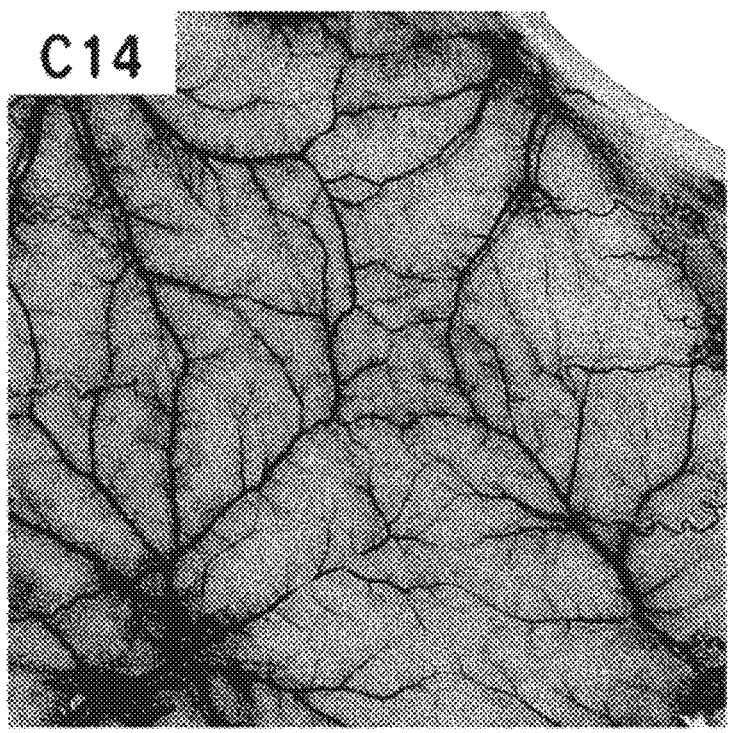
FIG. 6 is a photograph of the tissue into which a gel of 34C14 was implanted.

FIG. 5 shows a photograph of the tissue in the case PBS alone was injected in the same manner (control). FIG. 6 shows a photograph of the tissue in the case 34C14 was implanted (described as "C14" in the Figure).

According to FIGS. 5 and 6, it was found that the capillary density was clearly increased under conditions where the 34C14-ApGltn gel was implanted, as compared to PBS.

(Tissue Observation 2)

In the same manner as in the measurement of blood flow rate described above, 500 μl of a 34C12-ApGltn gel was implanted subcutaneously into the back of the mouse, and 3 days after, a tissue around the implanted site was extracted and observed.

Figure 7:
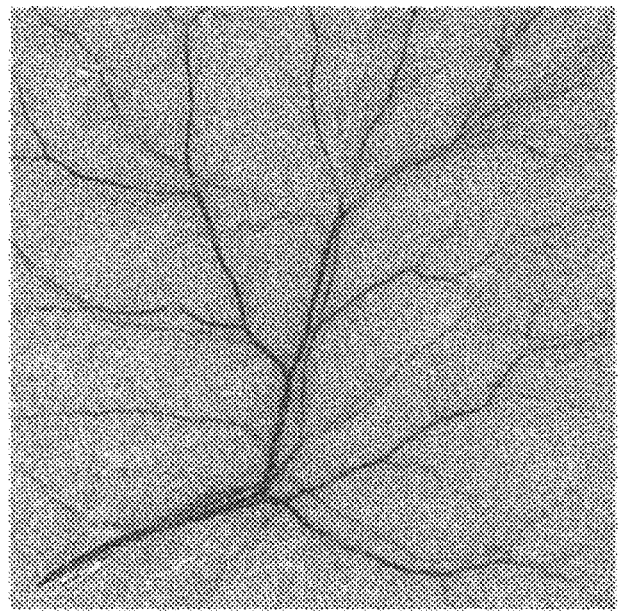
FIG. 7 is a photograph of the tissue into which PBS alone was injected.
Figure 8:
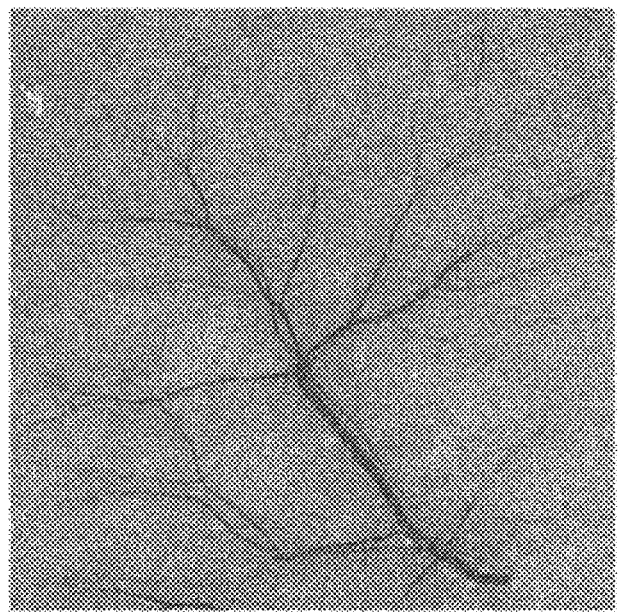
FIG. 8 is a photograph of the tissue into which a gel of the original gelatin (Org) was injected.
Figure 9:
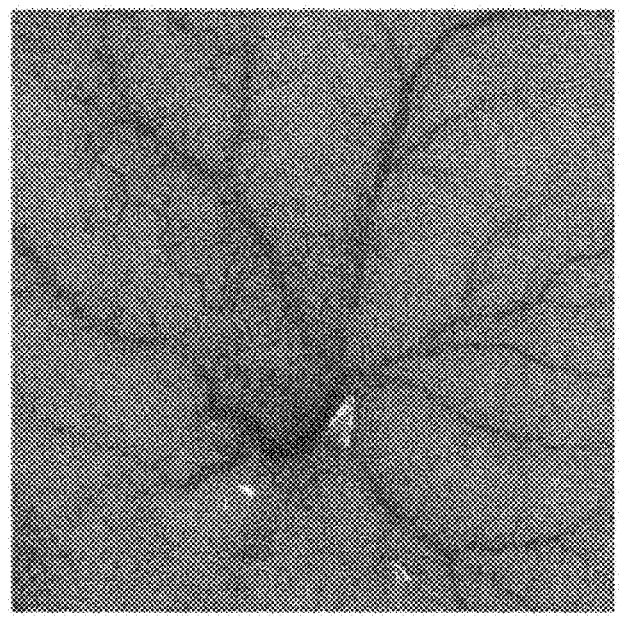
FIG. 9 is a photograph of the tissue into which a gel of 34C12 was implanted.

FIG. 7 shows a photograph of the tissue in the case PBS alone was injected in the same manner (control). FIG. 8 shows a photograph of the tissue in the case a gel the original gelatin (described as "Org" in the Figure) was injected in the same manner. FIG. 9 shows a photograph of the tissue in the case the 34C12-ApGltn gel (described as "34C12" in the Figure) was implanted.

As shown in FIGS. 7 to 9, compared to the tissue in the case PBS or a gel of the original gelatin was injected, the capillary density was clearly increased in the tissue in the case the 34C12-ApGltn gel was implanted.

(Tissue Images with HE Staining and Immunostaining)

Figure 10:
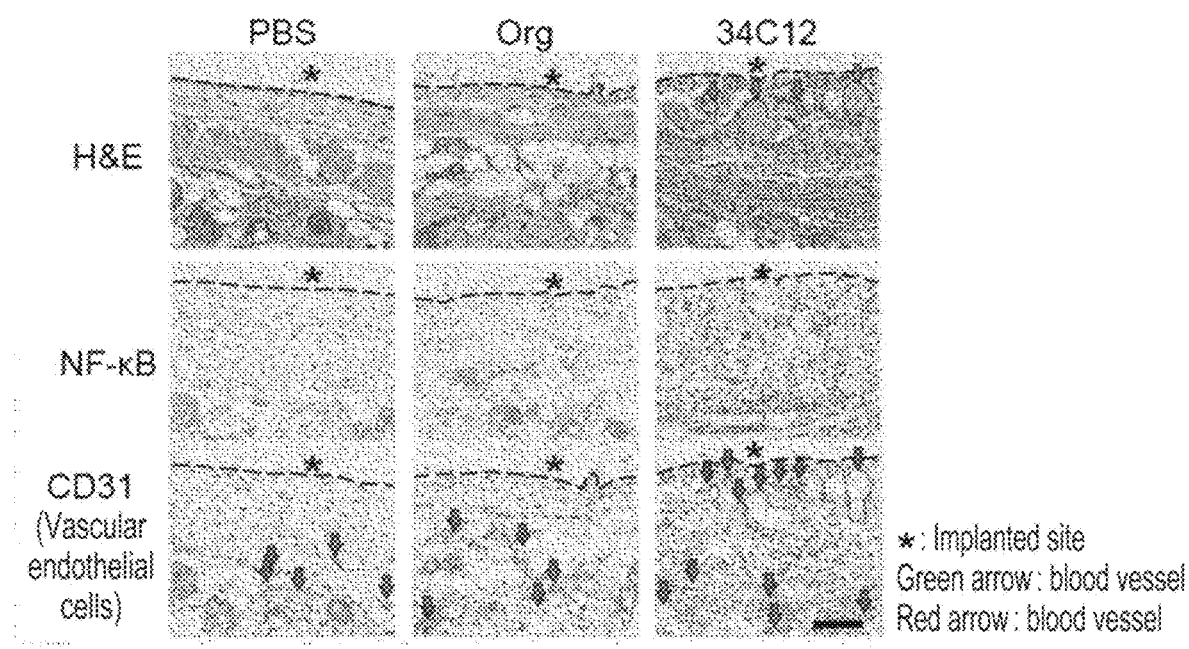
FIG. 10 shows HE stained-, NF-κB stained-, and CD31 stained images of the tissues into which a gel of 34C12 was implanted. Green arrows appended to the HE stained tissue image and red arrows appended to the CD31 immunostained tissue image indicate blood vessels.

In the same manner as in the measurement of blood flow rate described above, 500 μl of a 34C12-ApGltn gel was implanted subcutaneously into the back of the mouse, and 3 days after, a tissue around the implanted site was extracted. The obtained tissues were fixed with neutral buffered formalin, embedded with paraffin, and then sliced. The resulting sections were stained with hematoxylin-eosin staining (HE staining) and NF-κB and CD31 immunostaining (NF-κB was stained with an NF-κB antibody, and CD31 was stained with a CD31 antibody), and each stained tissue was observed with a microscope. The microscopic images of each stained tissue are shown in FIG. 10. The observation results are as follows:

1. HE Staining

No blood vessels and erythrocytes were observed in the tissue into which phosphate buffer (PBS) or a gel of the original gelatin (Org) was implanted, while blood vessels and erythrocytes were observed in the tissue into which the 34C12-ApGltn gel was implanted, confirming angiogenesis.

2. Immunostaining of NF-κB

No staining was observed in the tissue into which phosphate buffer (PBS) or a gel of the original gelatin (Org) was implanted, while stained was the tissue into which the 34C12-ApGltn gel was implanted (light brown portion), confirming angiogenesis by vascular endothelial cells, which NF-κB is involved in.

3. Immunostaining of CD31

Compared to tissues into which phosphate buffer (PBS) or the original gelatin (Org) was injected, the presence of more CD31 (light brown portion) was observed in the tissue into which the 34C12-ApGltn gel was implanted, confirming angiogenesis by vascular endothelial cells.

(Degradability)

To examine gel degradability in vitro, a degradation experiment was performed with collagenase.

First, each gel at a concentration of 200 mg/ml was placed in a 2.5 mL PP (polypropylene) tube, and 500 μl of PBS was added to swell. Next, after removing the excess PBS, 500 μl of 10 units/ml collagenase (a solution in Tris-HCl containing 2% $CaCl_2$) was added, and the mixture was incubated at 37° C.

After a certain period of time, the gel in PP tube was centrifuged at 10,000 rcf, and the supernatant was removed, and then the residual was weighed. This procedure was repeated, and the measurements were performed up to 8 hours.

Org, C6, and C18 were unmeasurable, because they were miscible with PBS. The results are shown in FIG. 11.

Figure 11:
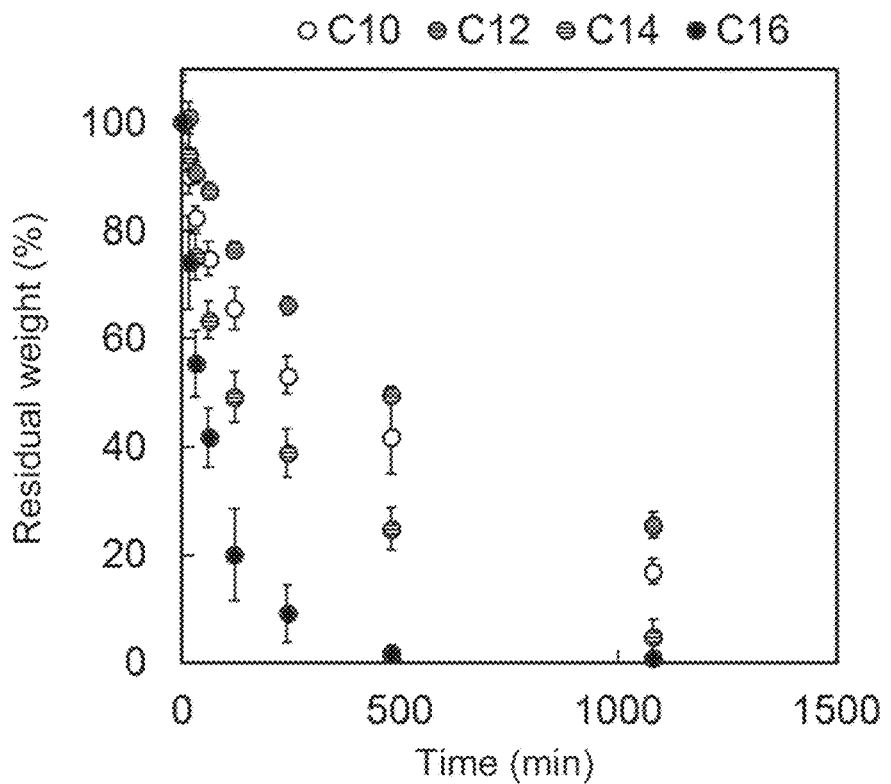
FIG. 11 shows the test results of gel degradability in vitro.

According to FIG. 11, the residues of C12 gel were significantly higher 8 hours after the degradation treatment, as compared to those in the other conditions.

Figure 12:
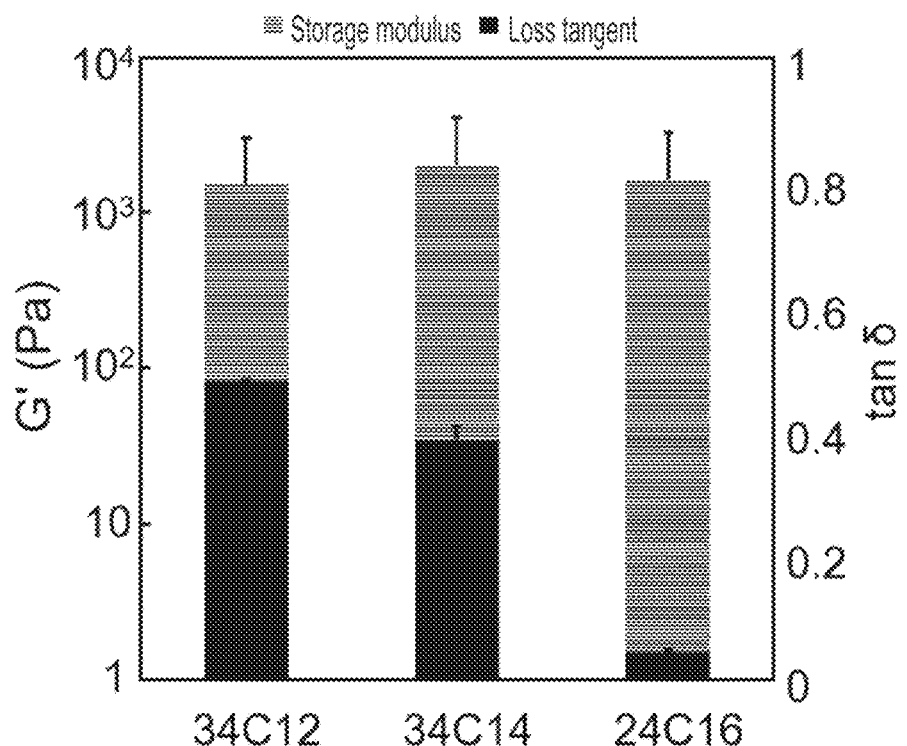
FIG. 12 shows the measurement results of storage modulus and tan δ of gels.

FIG. 12 shows storage modulus and tan δ as measured by the method described below. According to FIG. 12, there was no significant difference among the gels in terms of storage modulus, while as comparing the gels in terms of tan δ, there was a correlation between the degradation rate and tan δ, which is indicative of viscosity. Thus, it was considered that viscousness of gel suppressed the degradation and diffusion by collagenase.

In other words, it was found that when the sum of the carbon numbers of a hydrophobic group is 13 to 17 (preferably 14 to 16), the gel has excellent degradability.

(Injection Test)

Gels were prepared from each gelatin derivative of Examples 3 to 7 (C10, C12, C14, C16, and C18) and the original gelatin (Org) in the same manner as the measurement of blood flow rate described above, and then subjected to a test of extruding the gels with a syringe. The extrusion results are shown in FIG. 13.

As a gel is more easily extruded and more uniformly formed, the gel has a more excellent effect as a gel for promoting angiogenesis.

Figure 13:
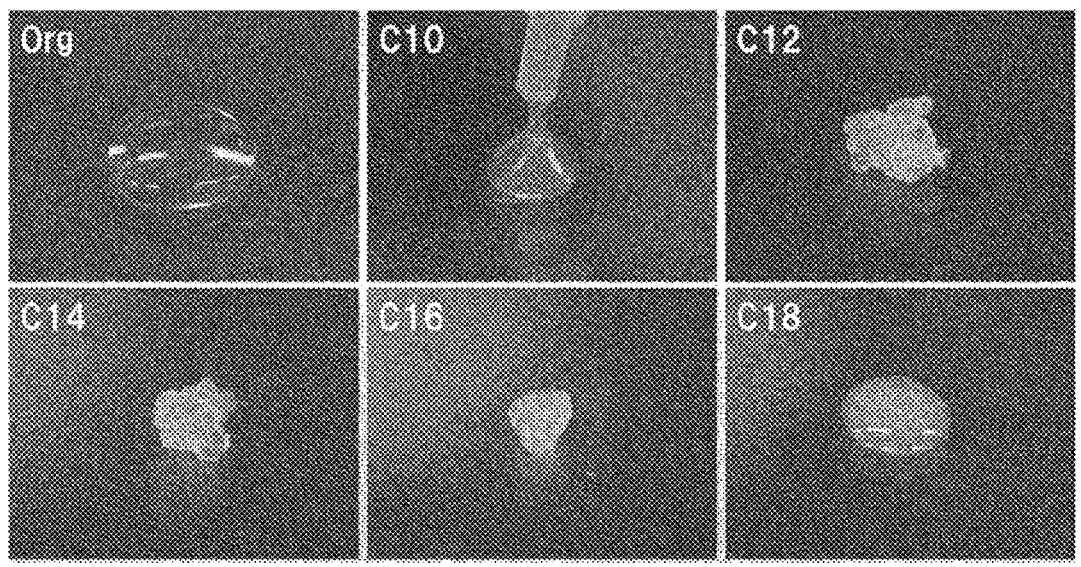
FIG. 13 shows the results of a gel injection test.

All of the gelatin derivatives of Examples 3 to 7 (C10, C12, C14, C16, and C18) were extrudable from a syringe and formed a uniform gel as shown in FIG. 13. Org was extrudable but failed to sufficiently form a gel.

C16 tended to form a gel more sufficiently as compared to C10. Furthermore, C16 tended to form a more uniform gel as compared to C18.

From the above, it was shown that when the sum of the carbon numbers of a hydrophobic group is 11 to 17, it is easier to form a gel; when 12 to 16, it is easier to form a more uniform gel; and when 13 to 16, it is more easier to inject a gel.

Examples 8 to 17

The gelatin derivatives 9C18, 56C16, 24C16, 12C16, 34C14, 16C14, 52C12, 34C12, 60C10, and 30C10 were prepared in the same manner as the gelatin derivative 19C12 described above, except that the linear alkylaldehydes of C18, C16, C14, C12, and C10 were respectively mixed into a gelatin solution in an amount corresponding to a derivatization rate of 150 mol % to the amino groups of gelatin, and 2-picoline borane at 1.5 equivalent molars to the added alkylaldehydes was added.

(Viscoelasticity Measurement)

Figure 14:
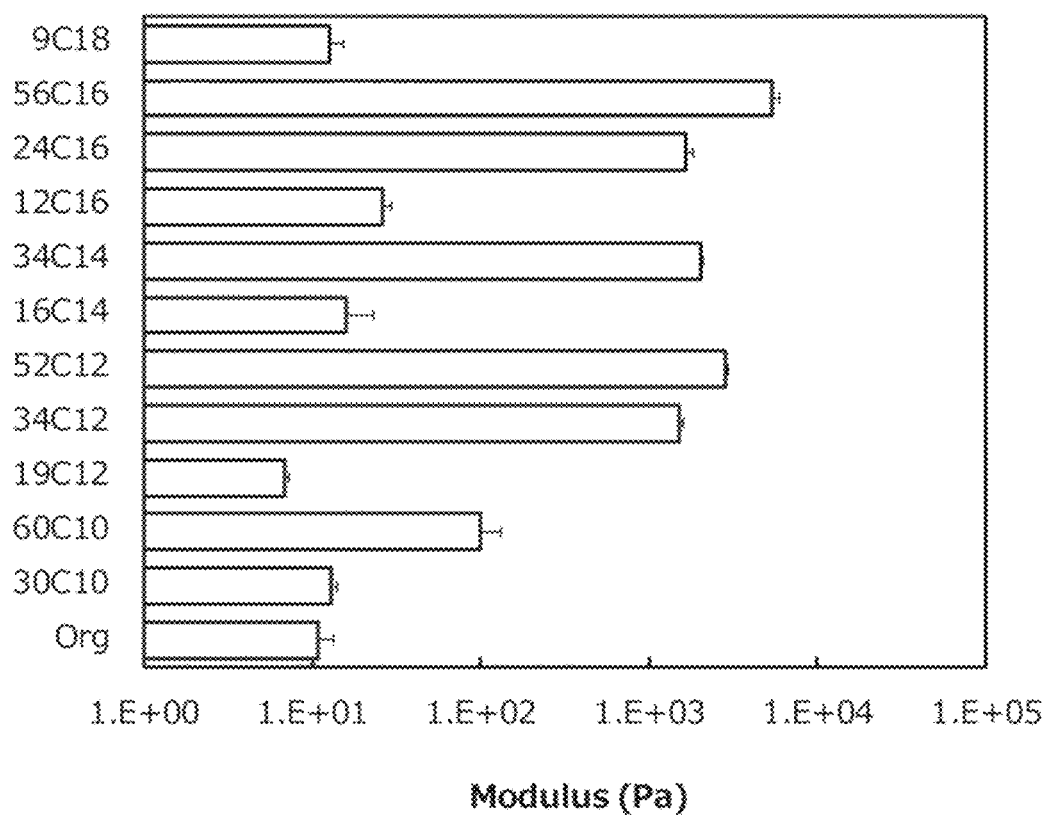
FIG. 14 shows the measurement results of storage modulus of gels.
Figure 15:
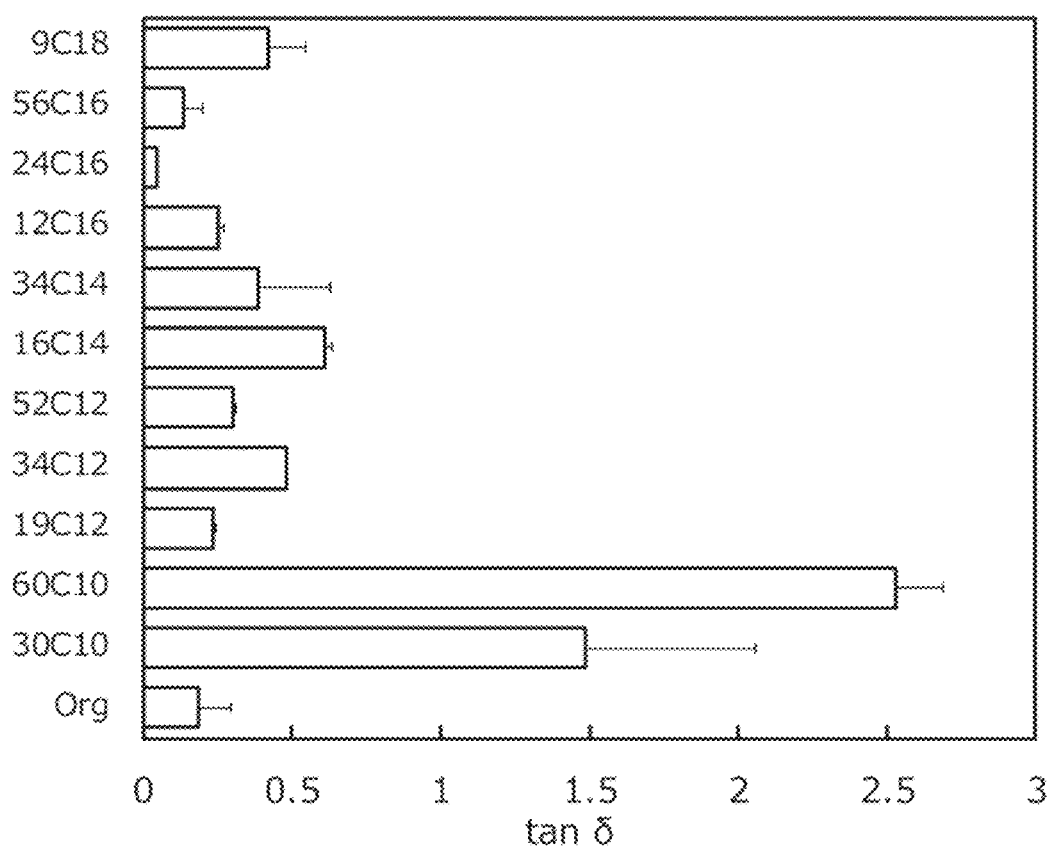
FIG. 15 shows the measurement results of tan δ of gels.

Gels were prepared from respective gelatin derivatives of Examples 1 and 8 to 17(19C12, 9C18, 56C16, 24C16, 12C16, 34C14, 16C14, 52C12, 34C12, 60C10, and 30C10) and the original gelatin (Org) in the same manner as the measurement of blood flow rate described above, and storage modulus (Pa) and tan δ were measured by the following methods. The results are shown in FIGS. 14, 15, and Table 2.

Test Conditions

Equipment used: dynamic viscoelasticity measuring device (MCR301, Anton Paar GmbH, Austria)

Sample shape: diameter 10 mm, thickness 1 mm

Angular frequency, strain, temperature: 0.1 to 100 Hz, 1%, 37° C.

TABLE 2

| | Storage modulus (Pa) | tan δ |
|---|---|---|
| Org | 11 | 0.18 |
| 30C10 | 13 | 1.49 |
| 60C10 | 99 | 2.53 |
| 19C12 | 7 | 0.23 |
| 34C12 | 1520 | 0.48 |
| 52C12 | 2850 | 0.30 |
| 16C14 | 16 | 0.61 |
| 34C14 | 2050 | 0.39 |
| 12C16 | 26 | 0.25 |
| 24C16 | 1657 | 0.05 |
| 56C16 | 5460 | 0.14 |
| 9C18 | 13 | 0.42 |

[Preparation of Crosslinked Gelatin Derivative]

Examples 18 to 20

100 g of gelatin (Mw=33,000, manufactured by Nitta Gelatin Inc.) derived from Alaska pollock was dissolved in 350 mL of water, and 140 mL of ethanol was added to the obtained aqueous solution, and the mixture was stirred at 50° C. Dodecanal ($C_{12}H_{24}O$) at 1.5 equivalent molars to the amino groups of gelatin, which is a stoichiometric amount corresponding to a derivatization rate of 150 mol %, was dissolved in 5 mL of ethanol, and mixed with the gelatin solution. Then, 2-picoline borane at about 1.5 equivalent molars to dodecanal were added, and the mixture was stirred for 18 hours. The reaction solution was added dropwise into cold ethanol at about 10 times the volume of the reaction solution to re-precipitate the resulting gelatin derivative, which was then subjected to suction filtration. The obtained precipitate was added to cold ethanol at about 5 times the volume of the resulting precipitate, washed with stirring for 1 hour and then subjected to suction filtration. After repeating this washing three times, the filtrate was dried under vacuum for 2 days to obtain a white gelatin derivative into which a dodecyl group was introduced in a yield of about 91.6 (mass/mass) %. The derivatization rate (introduction rate) was confirmed by a colorimetric method with trinitrobenzene sulfonic acid and found to be 33 mol % (0.33).

The gelatin derivative (33C12-ApGltn) obtained by the above was dissolved in ultrapure water at 50° C. such that the gelatin concentration was 5% by mass, thereby obtaining a gelatin solution. Then, the same volume of ethanol was added to the above aqueous solution to obtain a diluted solution. Next, the diluted solution was maintained at 50° C., installed in a spray dryer device (a mini spray dryer, B-290, manufactured by BÜCHI Labortechnik AG), and dried at 180° C. with adjusting the flow rate of the nitrogen gas to 440 L/h and the flow rate of the diluted solution to 410 mL/h to obtain an intermediate powder containing intermediate particles. The resulting intermediate powder was heated at 150° C. for 3 hours, 6 hours, or 9 hours to obtain crosslinked gelatin powders (Examples 19 to 21).

Figure 16:
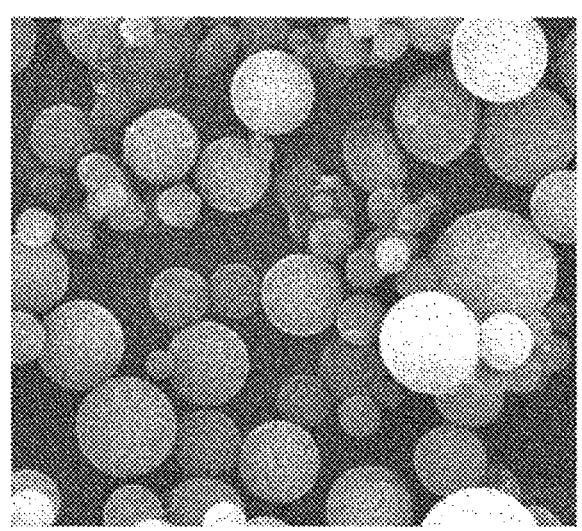
FIG. 16 is an electron micrograph of crosslinked original gelatin (Org) particles.
Figure 17:
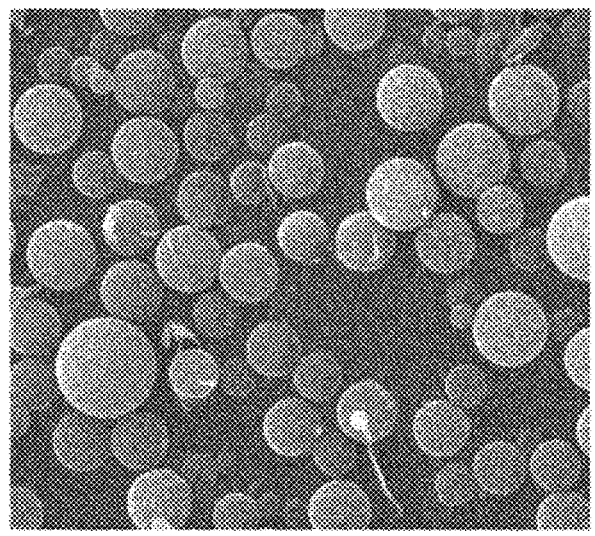
FIG. 17 is an electron micrograph of crosslinked 33C12 particles.

The original gelatin (Org) was similarly heated at 150° C. for 3 hours, 6 hours, or 9 hours to obtain crosslinked gelatin powders. FIG. 16 shows an electron micrograph of crosslinked particles obtained by heating the original gelatin (Org) for 3 hours, and FIG. 17 shows an electron micrograph of crosslinked particles obtained by heating 33C12-ApGltn for 3 hours. The crosslinked particles of 33C12-ApGltn obtained by heating for 3 hours had a more uniform particle size of 0.5 to 5 μm.

[Evaluation]

The following evaluation tests were performed for particles of the crosslinked gelatin derivative (33C12-ApGltn) obtained as described above.

(Measurement of Blood Flow Rate)

Phosphate buffered saline (PBS) was added to the crosslinked gelatin derivatives (33C12-ApGltn), which are different in crosslinking times, and crosslinked original gelatin (Org) to prepare 40% (mass/volume) hydrogels. The resulting hydrogels were respectively implanted subcutaneously into the back of the mice, and the blood flow rate was measured with a laser doppler blood flow meter. In the same way, PBS as a control and a sham as a comparison were each injected subcutaneously to the back of the mice, and the blood flow rate was measured with a laser doppler blood flow meter.

The gelatin derivatives and the original gelatin were respectively sterilized by irradiation with ultraviolet light in a powder state for 1 hour. 200 mg of each was dissolved in 500 μl of PBS, and then irradiated with UV for another 1 hour. Mice used were Hos: HR-1 hairless mice.

Figure 18:
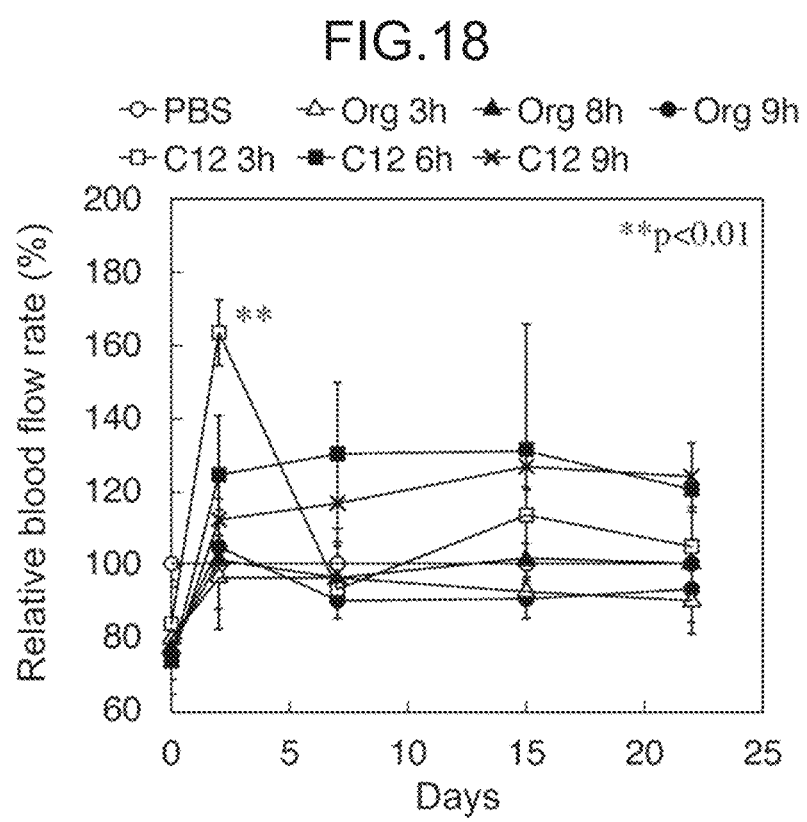
FIG. 18 is the quantification results of blood flow rate by laser doppler.

PBS, the sham and the hydrogels were injected by 250 μl into around the middle of the back of the mice under anesthesia. After 2, 7, 15 and 22 days, blood flow rate at the sample-implanted site was measured with a laser doppler blood flow meter. The measurement was performed after fixing the mouse respiration rate (3 times/sec) and laser gain (40) from day 2. The measurement results of the blood flow rate are shown in FIG. 18. The measured values are relative values where the blood flow rate of the sham on each measurement day is set to 100. All the blood flow rates of the powdery crosslinked gelatin derivative (33C12-ApGltn) prepared at the different crosslinking times were increased as compared to those of the sham in the corresponding crosslinking times. In particular, the blood flow rates of those prepared at the crosslinking times of 6 and 9 hours were highly increased. On the other hand, no similar effect was obtained when PBS alone was injected or when the crosslinked original gelatin was injected.

(Tissue Observation)

In the same manner as done to the tissue used for the measurement of blood flow rate described above, 50 μl of a hydrogel of each of the crosslinked gelatin derivative (33C12-ApGltn) and the crosslinked original gelatin (Org) obtained by heating for 3 hours was injected subcutaneously into the back of the mouse, and 2 days after, a tissue around the implanted site were extracted and observed.

Figure 19:
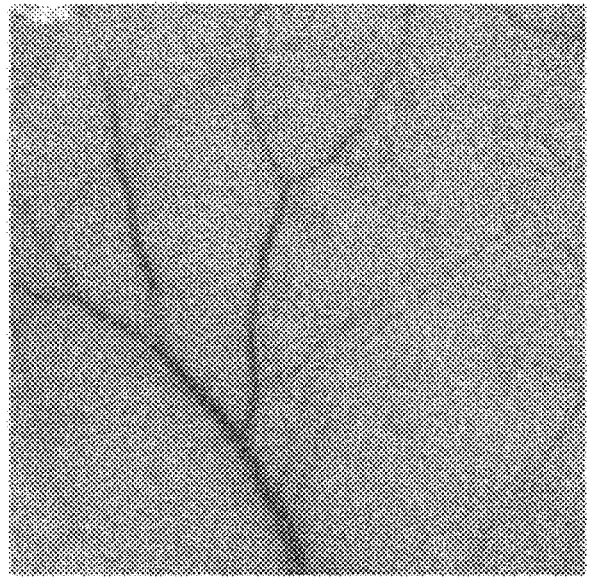
FIG. 19 is a photograph of the tissue into which PBS alone was injected.
Figure 20:
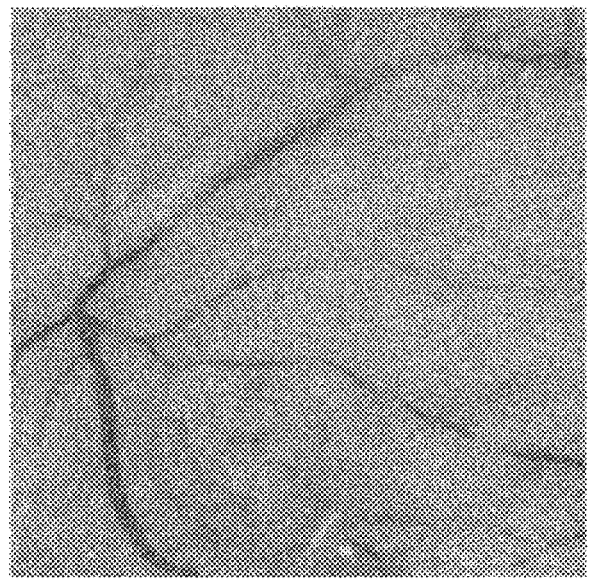
FIG. 20 is a photograph of a tissue around the site into which original gelatin (Org) was injected.
Figure 21:
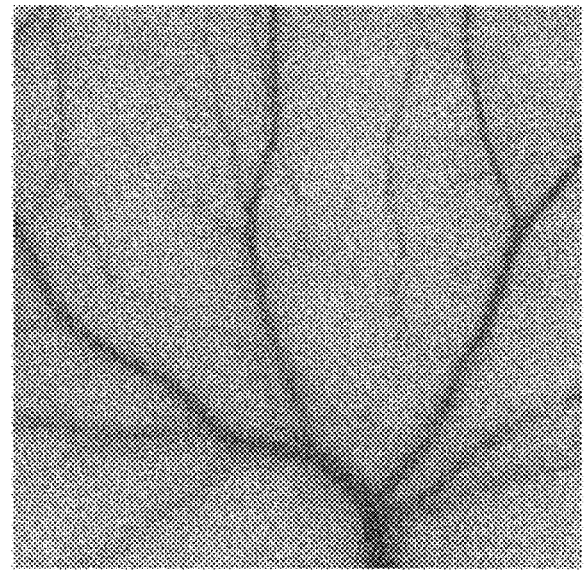
FIG. 21 is a photograph of a tissue around the site into which 33C12 was implanted.

FIG. 19 shows a photograph of the tissue into which PBS alone (control) was injected. FIG. 20 shows a photograph of the tissue into which the crosslinked original gelatin (described as "Org" in the Figure) was implanted. FIG. 21 shows a photograph of the tissue into which the crosslinked gelatin derivative 33C12-ApGltn (described as "33C12" in the Figure) was implanted.

As shown in FIGS. 19 to 21, compared to the tissue into which PBS was injected and the tissue into which the gel of the crosslinked original gelatin was injected, the capillary density was increased in the tissue into which the gel of the crosslinked 33C12-ApGltn was implanted.

[Preparation of Crosslinked Fiber Mesh]

Examples 21 to 24

First, the gelatin derivatives 41C8, 33C12, and 26C16 were prepared in the same manner as in Example 1, except that the linear alkylaldehydes of C8, C12, and C16 were respectively mixed into a gelatin solution in an amount corresponding to a derivatization rate of 150 mol % to the amino group of the gelatin, and 2-picoline borane at 1.5 equivalent molars to the added alkylaldehydes was added.

Figure 22:
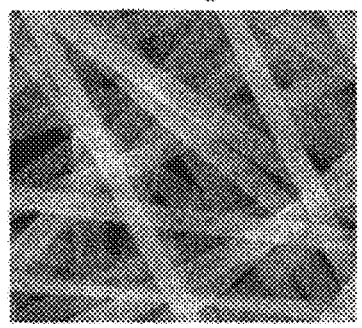
FIG. 22 is an electron micrograph of a fiber mesh of crosslinked original gelatin (Org).
Figure 23:
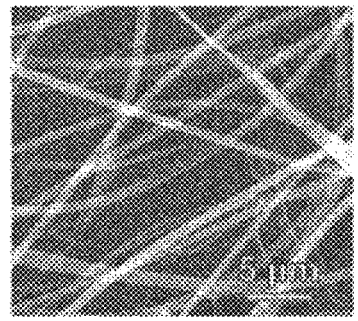
FIG. 23 is an electron micrograph of a fiber mesh of crosslinked 26C16.

Next, the obtained gelatin derivatives 41C8, 33C12, and 26C12 were dissolved in aqueous 20 to 50% ethanol solutions at a concentration of 15% (mass/volume). Then, a voltage of 30 kV was applied to a container containing the solution, while maintaining the solution at room temperature, with an electrospinning apparatus (nanofiber electrospinning apparatus NANON-03, manufactured by MEC, Inc.) to form fibers, and then the container was stood still to deposit the fibers to make a sheet. The resulting fiber mesh was heated at 150° C. for 4 hours under reduced pressure to introduce a crosslinked structure. FIG. 22 shows an electron micrograph of the crosslinked fiber mesh obtained from the original gelatin (Org). FIG. 23 shows an electron micrograph of the crosslinked fiber mesh obtained from 26C16-ApGltn. In the 26C16-ApGltn crosslinked fiber mesh, the sheet was formed with thinner uniform fibers having a fiber diameter of 1 to 5 μm.

[Evaluation]

(Measurement of Blood Flow Rate)

Into around the middle of the back of the mice under anesthesia, 250 μl of PBS and the sham, and each fiber mesh (of approximately circular with a diameter of 7 mm) were implanted. After 1, 2, and 3 days, the blood flow rate at the sample-implanted site was measured with a laser doppler blood flow meter. The blood flow rates on respective measurement days of the tissues into which each fiber mesh and PBS were injected, were determined as a relative value to the blood flow rate of the sham which was set as 100. The test results are shown in FIG. 24.

Figure 24:
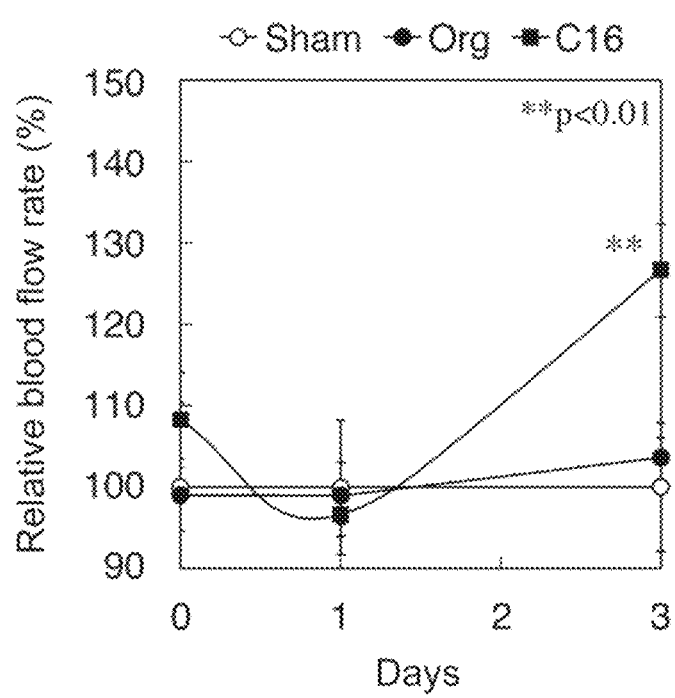
FIG. 24 is the quantification results of blood flow rate by laser doppler.

According to FIG. 24, when the fiber mesh according to the embodiment of the present invention was used, an increase in blood flow rate was observed on day 3 after the injection. Meanwhile, no such effect was obtained when PBS alone was injected or when the fiber mesh obtained from the crosslinked original gelatin was implanted.

(Tissue Observation)

Figure 25:
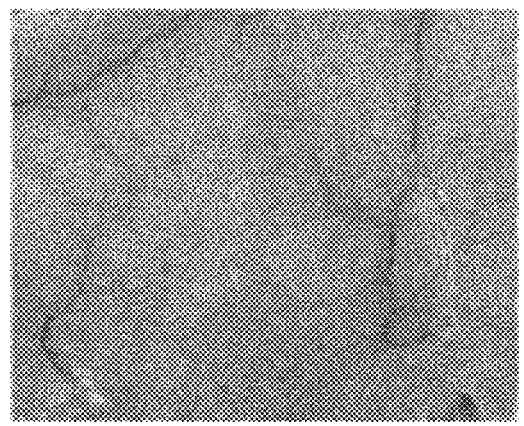
FIG. 25 is a photograph of a tissue around the site into which a sham was injected.
Figure 26:
FIG. 26 is a photograph of a tissue around the site into which a fiber mesh of crosslinked original gelatin (Org) was implanted.
Figure 27:
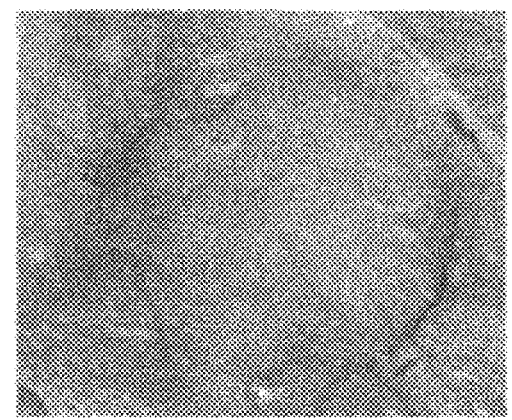
FIG. 27 is a photograph of a tissue around the site into which a fiber mesh of crosslinked 41C8 was implanted.
Figure 28:
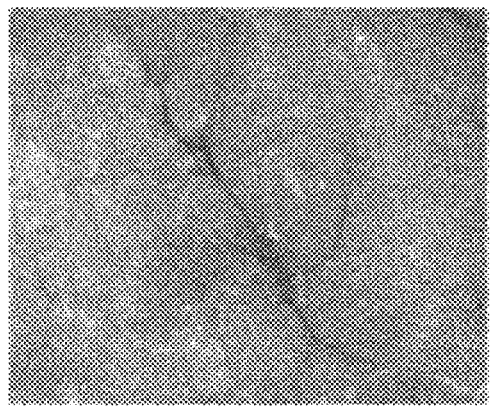
FIG. 28 is a photograph of a tissue around the site into which a fiber mesh of crosslinked 33C12 was implanted.
Figure 29:
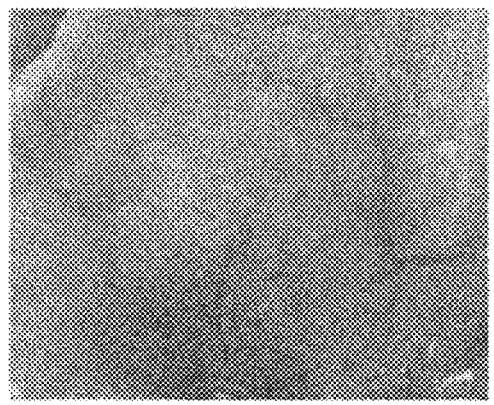
FIG. 29 is a photograph of a tissue around the site into which a fiber mesh of crosslinked 26C16 was implanted.

The obtained crosslinked fiber meshes of Examples 21 to 24 (41C8, 33C12, and 26C16), and the fiber mesh obtained from the crosslinked original gelatin and the sham were respectively implanted subcutaneously into the back of the mice, and 3 days after, the tissues around the implanted sites were extracted and observed. FIG. 25 shows a photograph of the tissue into which the sham was implanted. FIG. 26 shows a photograph of the tissue into which the original gelatin crosslinked fiber mesh (described as "Org" in the Figure) was implanted. FIG. 27 shows a photograph of the tissue into which the 41C8 crosslinked fiber mesh (described as "41C8" in the Figure) was implanted. FIG. 28 shows a photograph of the tissue into which the 33C12 crosslinked fiber mesh (described as "33C12" in the Figure) was implanted. FIG. 29 shows a photograph of the tissue into which the 26C16 crosslinked fiber mesh (described as "26C16" in the Figure) was implanted.

According to FIGS. 25 to 29, compared to the tissues into which the sham and the original gelatin crosslinked fiber mesh were implanted, the capillary density was increased in the tissues into which the 41C8 crosslinked fiber mesh, the 33C12 crosslinked fiber mesh, and the 26C16 crosslinked fiber mesh were implanted.

The invention claimed is:

1. A method for promoting angiogenesis in a mammal subject with a peripheral artery disease, comprising administering to the mammal subject a pharmaceutically effective amount of an angiogenesis promoter comprising at least one compound selected from the group consisting of a gelatin derivative of formula (1) and a crosslinked product of the gelatin derivative,

wherein Gltn is a gelatin residue;
L is a single bond or a divalent linking group;
$R^1$ and $R^2$ are each independently a hydrogen atom, or a hydrocarbon group having from 1 to 20 carbon atoms, provided that at least one of $R^1$ and $R^2$ is a hydrocarbon group;
wherein the angiogenesis promoter is free of a growth factor; and
wherein the peripheral artery disease is treated.

2. The method according to claim 1, wherein the hydrocarbon group is at least one group selected from the group consisting of a linear hydrocarbon group having 2 to 20 carbon atoms, an alicyclic hydrocarbon having 2 to 20 carbon atoms, an aromatic hydrocarbon group having 6 to 14 carbon atoms, and a combination group thereof having 2 to 20 carbon atoms.

3. The method according to claim 1, wherein the gelatin derivative or the crosslinked product is derived from a cold-water fish.

4. The method according to claim 3, wherein the cold-water fish is a cod.

5. The method according to claim 1, wherein the crosslinked product is administered as an active ingredient.

6. The method according to claim 1, wherein the angiogenesis promoter is in a form of a fiber mesh.

7. The method according to claim 1, wherein the angiogenesis promoter is in a form of particles.

* * * * *